US012360351B2

(12) United States Patent
Segev et al.

(10) Patent No.: US 12,360,351 B2
(45) Date of Patent: Jul. 15, 2025

(54) SYSTEM AND METHOD TO AUTOMATICALLY ADJUST ILLUMINATION DURING A MICROSURGICAL PROCEDURE

(71) Applicant: BEYEONICS SURGICAL LTD., Haifa (IL)

(72) Inventors: Eran Segev, Haifa (IL); Shahaf Zommer, Haifa (IL); Ron Schneider, Haifa (IL); Rani Ben Yishai, Haifa (IL)

(73) Assignee: BEYEONICS SURGICAL LTD, Haifa (IL)

( * ) Notice: Subject to any disclaimer, the term of this patent is extended or adjusted under 35 U.S.C. 154(b) by 453 days.

(21) Appl. No.: 17/287,552

(22) PCT Filed: Oct. 23, 2019

(86) PCT No.: PCT/IL2019/051140
§ 371 (c)(1),
(2) Date: Apr. 22, 2021

(87) PCT Pub. No.: WO2020/084611
PCT Pub. Date: Apr. 30, 2020

(65) Prior Publication Data
US 2021/0325649 A1    Oct. 21, 2021

(30) Foreign Application Priority Data
Oct. 25, 2018    (IL) .......................................... 262619

(51) Int. Cl.
*G02B 21/00*    (2006.01)
*A61B 3/00*    (2006.01)
*G02B 21/06*    (2006.01)

(52) U.S. Cl.
CPC ........ *G02B 21/0012* (2013.01); *A61B 3/0008* (2013.01); *G02B 21/06* (2013.01)

(58) Field of Classification Search
CPC .. G02B 21/0012; G02B 21/06; G02B 21/082; G02B 21/365; A61B 3/0008; A61B 90/30; A61B 90/20; G06F 3/013
See application file for complete search history.

(56) References Cited

U.S. PATENT DOCUMENTS 6,243,197 B1    6/2001    Schalz
6,830,334 B2    12/2004    Niven et al.
(Continued)

FOREIGN PATENT DOCUMENTS

EP    3285107 A1    2/2018
KR    20160148889 A    12/2016
WO    2017141187 A1    8/2017

*Primary Examiner* — Scott M. Getzow
(74) *Attorney, Agent, or Firm* — S.J. Intellectual Property Ltd.

(57) ABSTRACT

A surgical microscope lighting control system comprising a controller configured to: estimate or determine a lighting need of a surgeon during at least part of a surgical procedure based at least on a viewing status of a region of illumination, wherein the viewing status of the region of illumination is estimated or determined (a) based at least on whether or not the region of illumination is being displayed, or (b) based at least on tracking data of the surgeon or a head-mounted display; determine an adjustment to be made to an illumination provided by a lighting unit of a surgical microscope based on the lighting need; and in response to determining the adjustment, send a first signal to the lighting unit to change the illumination according to the adjustment.

20 Claims, 10 Drawing Sheets

(56) References Cited

U.S. PATENT DOCUMENTS

| | | | |
|---|---|---|---|
| 6,898,004 B2 | 5/2005 | Shimizu et al. | |
| 2002/0087149 A1 | 7/2002 | McCarry | |
| 2010/0201944 A1 | 8/2010 | Lewis et al. | |
| 2011/0261184 A1 | 10/2011 | Mason | |
| 2014/0015948 A1 | 1/2014 | Tam | |
| 2014/0346957 A1 | 11/2014 | Micucci et al. | |
| 2016/0262605 A1 | 9/2016 | Taylor et al. | |
| 2017/0020627 A1* | 1/2017 | Tesar | A61B 90/361 |
| 2018/0021101 A1 | 1/2018 | Abt | |
| 2018/0049811 A1* | 2/2018 | Themelis | A61B 34/25 |
| 2018/0140373 A1 | 5/2018 | Dos Santos et al. | |
| 2018/0147087 A1 | 5/2018 | Bacher et al. | |

\* cited by examiner

SYSTEM AND METHOD TO AUTOMATICALLY ADJUST ILLUMINATION DURING A MICROSURGICAL PROCEDURE

TECHNICAL FIELD

The present disclosure generally relates to adjusting illumination of a surgical microscope during a surgical procedure.

BACKGROUND

Many ophthalmic devices illuminate visible light for diagnosing or treating ocular pathologies. This illumination might be hazardous to the eyes under prolonged exposures and may also lead to patient discomfort. One of the most common hazards is the hazard of phototoxicity, caused by blue light (visible light in the wavelength band of 380 nm-500 nm) irradiating the retina. The safety standards set recommended limits for the irradiation levels and total energy of this illumination, but also acknowledge the reality that occasionally surgeons or clinicians may have to exceed those limits to complete an examination or procedure.

Other body parts, for example, but not limited to, the brain, may also be sensitive to light (e.g., heat produced by light or phototoxicity) during surgery. Additionally, illumination is frequently adjusted by a surgeon for other reasons during a medical procedure.

References considered to be relevant as background to the presently disclosed subject matter are listed below. Acknowledgement of the references herein is not to be inferred as meaning that these are in any way relevant to the patentability of the presently disclosed subject matter.

U.S. Pat. No. 6,898,004 to Shimizu, et al., describes a microscope system wherein illumination light rays are emitted from a light source. The illumination light rays are collimated and reflected from a mirror to the optical element array. The optical element array is located at a conjugate position of a specimen, and includes a plurality of micro mirrors arranged in a matrix form. The micro mirrors are individually controlled to selectively reflect the illumination light rays for illuminating the specimen. Thus, a predetermined pattern of the light rays is reflected from the optical element array to an objective lens. The illumination light rays are projected on the specimen from the objective lens and the specimen is illuminated by the predetermined illumination pattern.

U.S. Pat. No. 6,243,197 to Schalz describes an illuminating device for a microscope, having a light source, an illuminating optical system and an LCD arranged in the illuminating beam path. The illuminating light is directed onto the object from the light source via the LCD, a transparent/opaque pattern being generated on the LCD by means of a control and calculating device. The LCD is arranged in a plane (AP') which is conjugate with respect to the field diaphragm plane or aperture diaphragm plane (AP) and has a planar matrix composed of individual pixels arranged next to one another and of the same dimensions, the pixels each being constructed such that they can be driven individually to generate an arbitrary transparent/opaque pattern. The control and calculating device is constructed as a computer with a graphics card. The graphics card generates the image signal for driving the LCD, it being possible for the image generated on the LCD to be represented simultaneously on a separate monitor.

US Patent Publication serial number 20020087149 of McCary describes an ophthalmic illumination device which includes a source of light that has a spectrum primarily in a red spectrum and is substantially devoid of spectra in any other color, including a blue spectrum and a green spectrum. The red light is provided by a red light emitting diode and may be used in combination with known ophthalmic illumination devices that provide a white light. A surgeon controls the device and can switch between the red light and the white light.

International Patent Publication serial number WO2017141187 of Novartis Ag. describes methods and systems for performing an ophthalmic surgical procedure include pulsed illumination of target tissue. The systems may include an illumination instrument arranged to illuminate tissue at a surgical site during the ophthalmic surgical procedure. A light source provides illumination to the illumination instrument for emission from the illumination instrument toward the surgical site. A controller communicates with the light source and activates the light source to provide illumination pulses at a frequency above the flickering perception in humans and with enough light for cameral exposure and human light perception. The light source pulses to minimize phototoxicity.

BRIEF DESCRIPTION OF THE DRAWINGS

The present disclosure will be understood and appreciated more fully from the following detailed description, taken in conjunction with the drawings in which.

DESCRIPTION OF EXAMPLE EMBODIMENTS

Overview

Figure 1A:
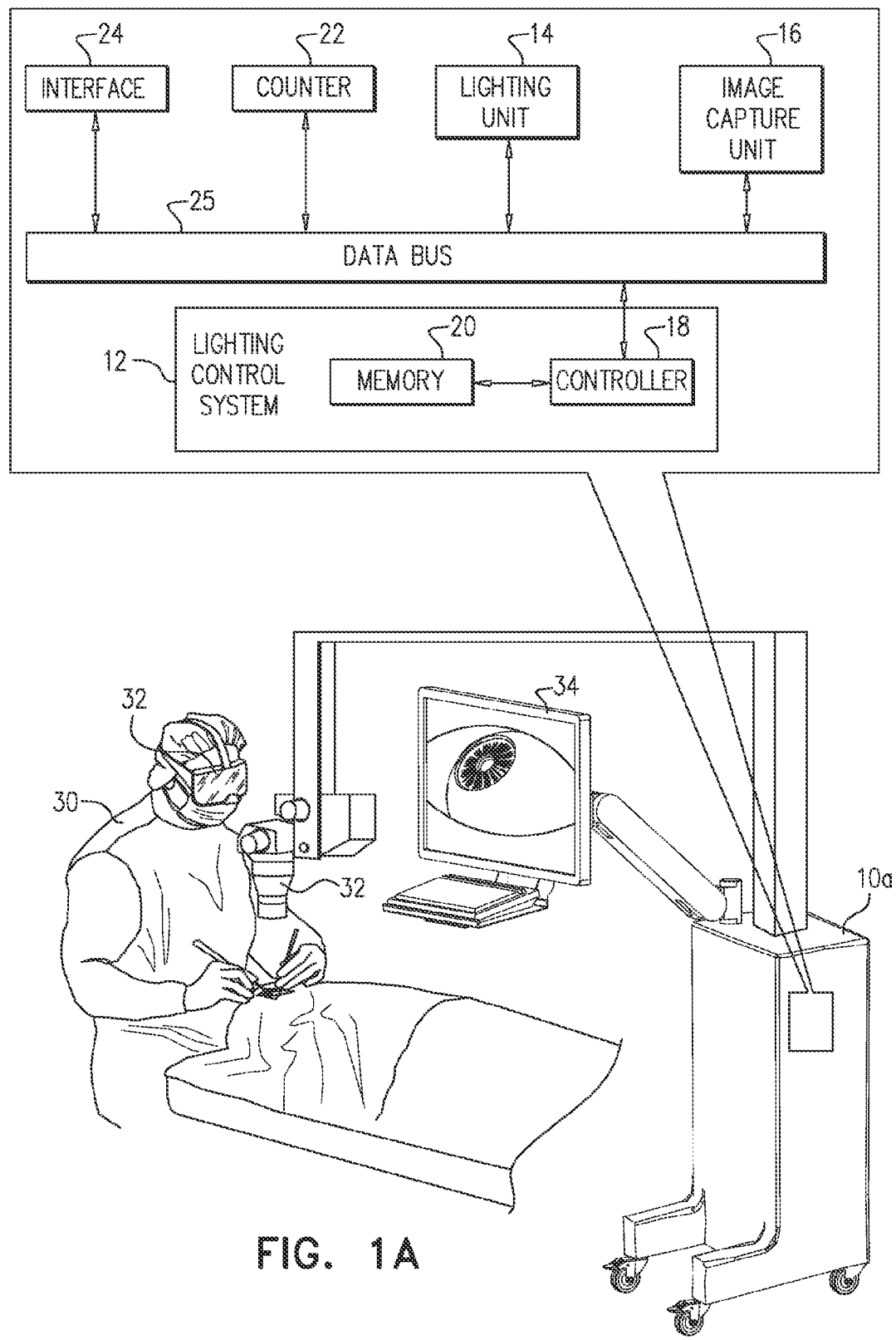
FIGS. 1a and 1b are partly pictorial, partly block diagram views of a surgical microscope system constructed and operative according to embodiments of the present disclosure.

In accordance with a first aspect of the presently disclosed subject matter, there is provided a surgical microscope lighting control system comprising a controller configured to: estimate or determine a lighting need of a surgeon during at least part of a surgical procedure based at least on a viewing status of a region of illumination, wherein the viewing status of the region of illumination is estimated or determined (a) based at least on whether or not the region of illumination is being displayed, or (b) based at least on tracking data of the surgeon or a head-mounted display; determine an adjustment to be made to an illumination provided by a lighting unit of a surgical microscope based on the lighting need; and in response to determining the adjustment, send a first signal to the lighting unit to change the illumination according to the adjustment.

In some cases, the viewing status of the region of illumination is estimated or determined based at least on whether or not the region of illumination is being displayed on the head-mounted display, or whether or not the region of illumination is being displayed on a monitor.

In some cases, the region of illumination is a sub-portion of an illuminated area.

In some cases, the viewing status of the region of illumination is of the surgeon viewing the region of illumination or not viewing the region of illumination.

In some cases, the tracking data includes any one or more of the following: a position of a head or the head-mounted display; a rate of movement of the head or the head-mounted display; an orientation of the head or the head-mounted display; or eye gaze data.

In some cases, the tracking data indicates that the region of illumination is not being viewed by the surgeon when the tracking data indicates any one or more of the following: head movements greater than a given rate; the surgeon is looking outside of the region of illumination or outside of given angular boundaries; the head-mounted display is not moving as it is not being worn; the head-mounted display is stowed; the surgeon is peeking around the head-mounted display away from the region of illumination; and the surgeon has stepped away from a given region where the surgical procedure is taking place.

In some cases, the tracking data indicates that the region of illumination is being viewed by the surgeon when the tracking data indicates any one or more of the following: the surgeon is looking at the region of illumination or inside of given angular boundaries; the surgeon is peeking around the head-mounted display but in the region of illumination; and the head-mounted display is stowed or is not being worn, but the surgeon is looking at the region of illumination.

In some cases, the given angular boundaries are surgeon-specific.

In some cases, the controller is further configured to: use eye gaze data comprised within the tracking data to determine where the surgeon is looking within the region of illumination; and estimate or determine based on where the surgeon is looking, how to adjust a current illumination provided by the lighting unit.

In some cases, the tracking data includes proximity data obtained by a proximity sensor or by a touch sensor, and wherein the controller is further configured to estimate or determine the viewing status of the region of illumination based at least on the proximity data providing an indication of whether or not the surgeon is in proximity to an eyepiece of the surgical microscope.

In some cases, the system further comprises at least one first sensor, the at least one first sensor viewing at least part of the region of illumination.

In some cases, the controller is further configured to: analyze at least the region of illumination within at least one images captured by the at least one first sensor to detect movement and/or surgical tools; and estimate or determine the viewing status of the region of illumination based at least on the movement, and/or a presence or an absence of the surgical tools in at least the region of illumination.

In some cases, the controller is further configured to: analyze at least one image captured by the at least one first sensor to determine whether a body part is included in the at least one image; and estimate or determine the viewing status based at least on whether the body part is included in the at least one image.

In some cases, the controller is further configured to provide an indication of at least one amount of at least one radiation spectrum that has been irradiated on a first body part during at least one time period.

In some cases, the indication includes any one or more of the following: a recorded message; an audible indication; and one, or a combination of two or more of: a textual or numeric or symbolic indicator displayed in the head-mounted display or on a monitor.

In some cases, the adjustment includes changing an intensity of the illumination provided by the lighting unit.

In some cases, the system further comprises the lighting unit, which is configured to change the intensity of the illumination using any one or more of the following: adjusting an optical element disposed in the optical path of the lighting unit to change the size of the spot of light; modifying the temporal pattern of the illumination with pulsing radiation; electrically controlling a permanent liquid crystal shutter disposed in an optical path of the lighting unit.

In some cases, the adjustment includes changing a spectrum of radiation of the illumination provided by the lighting unit.

In some cases, the system further comprises the lighting unit, which is configured to change the spectrum of radiation of the illumination using any one or more of the following: a band-pass filter, a long-pass filter; a dichroic mirror; and switching between two sources of illumination having different radiation spectra.

In some cases, the adjustment includes switching between flood illumination and coaxial illumination.

In some cases, the adjustment includes modifying a spatial pattern of the illumination.

In some cases, modifying the spatial pattern of the illumination includes changing the intensity of the illumination of a first part of the region of illumination while leaving the illumination of a second part of the region of illumination unchanged.

In some cases, modifying the spatial pattern of the illumination includes changing a spectrum of radiation incident on a first part of the region of illumination while leaving the spectrum of radiation incident on a second part of the region of illumination unchanged.

In some cases, the system further comprises the lighting unit which includes a dynamic light masking device configured to modify the spatial pattern of the illumination.

In some cases, the dynamic light masking device includes any one or more of the following to at least partially modify the pattern of illumination: a digital mirror device; a digital mirror device in an optical path of two radiation sources to selectively select between the two radiation sources; a spatial light modulator; a movable spatial filter or mask; a holographic mask, and a liquid crystal shutter.

In some cases, in response to determining the adjustment, the controller is configured to send a second signal to at least one image capture unit of the surgical microscope to compensate for the adjustment by any one or more of the following: adjusting an opening of a shutter of the image capture unit; increasing an integration time of the image capture unit; and increasing a gain of the image capture unit.

In accordance with a second aspect of the presently disclosed subject matter, there is provided a surgical microscope lighting control method, comprising: estimating or determining a lighting need of a surgeon during at least part of a surgical procedure based at least on a viewing status of a region of illumination by the surgeon, wherein the viewing status of the region of illumination is estimated or determined (a) based at least on whether or not the region of illumination is being displayed, or (b) based at least on tracking data of the surgeon or a head-mounted display; determining an adjustment to be made to an illumination provided by a lighting unit of a surgical microscope based on the lighting need; and in response to determining the adjustment, sending a first signal to the lighting unit to change the illumination according to the adjustment.

In some cases, the viewing status of the region of illumination is estimated or determined based at least on whether or not the region of illumination is being displayed on the head-mounted display, or whether or not the region of illumination is being displayed on a monitor.

In some cases, the region of illumination is a sub-portion of an illuminated area.

In some cases, the viewing status of the region of illumination is of the surgeon viewing the region of illumination or not viewing the region of illumination.

In some cases, the tracking data includes proximity data obtained by a proximity sensor or by a touch sensor, and wherein the method further comprises: estimating or determining the viewing status of the region of illumination based at least on the proximity data providing an indication of whether or not the surgeon is in proximity to an eyepiece of the surgical microscope.

In some cases, the tracking data indicates that the region of illumination is not being viewed by the surgeon when the tracking data indicates any one or more of the following: head movements greater than a given rate; the surgeon is looking outside of the region of illumination or outside of given angular boundaries; the head-mounted display is not moving as it is not being worn; the head-mounted display is stowed; the surgeon is peeking around the head-mounted display away from the region of illumination; and the surgeon has stepped away from a given region where the surgical procedure is taking place.

In some cases, the tracking data indicates that the region of illumination is being viewed by the surgeon when the tracking data indicates any one or more of the following: the surgeon is looking at the region of illumination or inside of given angular boundaries; the surgeon is peeking around the head-mounted display but in the region of illumination; and the head-mounted display is stowed or is not being worn, but the surgeon is looking at the region of illumination.

In some cases, the method further comprises: using eye gaze data comprised within the tracking data to determine where the surgeon is looking within the region of illumination; and estimating or determining based on where the surgeon is looking, how to adjust a current illumination provided by the lighting unit.

In some cases, the surgical microscope further comprises at least one first sensor, the at least one first sensor viewing at least part of the region of illumination.

In some cases, the method further comprises: analyzing at least the region of illumination within at least one image captured by the at least one first sensor to detect movement and/or surgical tools; and estimating or determining the viewing status of the region of illumination based at least on the movement, and/or a presence or an absence of the surgical tools in at least the region of illumination.

In some cases, the method further comprises: analyzing at least one image captured by the at least one first sensor to determine whether a body part is included in the at least one image; and estimating or determining the viewing status based at least on whether the body part is included in the at least one image.

In some cases, the method further comprises providing an indication of at least one amount of at least one radiation spectrum that has entered a first body part during at least one time period with respect to at least one limit of allowed radiation in accordance with a standard.

In some cases, the indication includes any one or more of the following: a recorded message; an audible indication; and one, or a combination of two or more of: a textual or numeric or symbolic indicator displayed in the head-mounted display or on a monitor.

In some cases, the adjustment includes changing an intensity of the illumination provided by the lighting unit.

In some cases, the changing the intensity of the illumination is performed using any one or more of the following: adjusting an optical element disposed in the optical path of the lighting unit to change the size of the spot of light; modifying the temporal pattern of the illumination with pulsing radiation; electrically controlling a permanent liquid crystal shutter disposed in an optical path of the lighting unit.

In some cases, the adjustment includes modifying a spatial pattern of the illumination; and modifying the spatial pattern of the illumination includes changing the intensity of the illumination of a first part of the region of illumination while leaving the illumination of a second part of the region of illumination unchanged.

In some cases, the adjustment includes modifying a spatial pattern of the illumination; and modifying the spatial pattern of the illumination includes changing a spectrum incident on a first part of the region of illumination while leaving the spectrum incident on a second part of the region of illumination unchanged.

In accordance with a third aspect of the presently disclosed subject matter, there is provided a software product, comprising a non-transient computer-readable medium in which program instructions are stored, which instructions, when read by a central processing unit (CPU), cause the CPU to: estimate or determine a lighting need of a surgeon during at least part of a surgical procedure based at least on a viewing status of a region of illumination, wherein the viewing status of the region of illumination is estimated or determined (a) based at least on whether or not the region of illumination is being displayed, or (b) based at least on tracking data of the surgeon or a head-mounted display; determine an adjustment to be made to an illumination provided by a lighting unit of a surgical microscope based on the lighting need; and in response to determining the adjustment, send a first signal to the lighting unit to change the illumination according to the adjustment.

In accordance with a fourth aspect of the presently disclosed subject matter, there is provided a surgical microscope lighting control system comprising: a counter configured to count at least one amount of at least one radiation spectrum that has entered a first body part during at least one time period during a surgical procedure; and a controller configured to provide, to an output device, an indication of the at least one amount of the at least one radiation spectrum that has entered the first body part during the at least one time period with respect to at least one limit of allowed radiation in accordance with a standard.

In some cases, the controller is further configured to analyze at least one image provided by a surgical microscope to determine if the first body part is included in the image and determine when the first body part is being illuminated.

In some cases, the indication includes any one or more of the following: a recorded message; an audible indication; and one, or a combination of two or more of: a textual or numeric or symbolic indicator displayed in the head-mounted display or on a monitor.

In accordance with a fifth aspect of the presently disclosed subject matter, there is provided a surgical microscope lighting control system comprising a controller configured to: estimate or determine a lighting need of a surgeon during at least part of a surgical procedure based at least on an image analysis related to the region of illumination viewed by at least one first sensor, wherein the image analysis includes any one or more of: (a) motion detection for detecting motion within the region of illumination; and/or (b) tool detection for detecting surgical tools within the region of illumination; determine an adjustment to be made to an illumination provided by a lighting unit of a surgical microscope based on the lighting need; and in response to determining the adjustment, send a first signal to the lighting unit to change the illumination according to the adjustment.

In accordance with a sixth aspect of the presently disclosed subject matter, there is provided a surgical microscope lighting control method, comprising: estimating or determining a lighting need of a surgeon during at least part of a surgical procedure based at least on an image analysis related to the region of illumination viewed by at least one first sensor, wherein the image analysis includes any one or more of: (a) motion detection for detecting motion within the region of illumination; and/or (b) tool detection for detecting surgical tools within the region of illumination; determining an adjustment to be made to an illumination provided by a lighting unit of a surgical microscope based on the lighting need; and in response to determining the adjustment, sending a first signal to the lighting unit to change the illumination according to the adjustment.

In accordance with a seventh aspect of the presently disclosed subject matter, there is provided a software product, comprising a non-transient computer-readable medium in which program instructions are stored, which instructions, when read by a central processing unit (CPU), cause the CPU to: estimate or determine a lighting need of a surgeon during at least part of a surgical procedure based at least on an image analysis related to the region of illumination viewed by at least one first sensor, wherein the image analysis includes any one or more of: (a) motion detection for detecting motion within the region of illumination; and/or (b) tool detection for detecting surgical tools within the region of illumination; determine an adjustment to be made to an illumination provided by a lighting unit of a surgical microscope based on the lighting need; and in response to determining the adjustment, send a first signal to the lighting unit to change the illumination according to the adjustment.

DETAILED DESCRIPTION

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

The terms "computer", "processor", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

In practice, some or all of the functions described herein may be combined in a single physical component or, alternatively, implemented using multiple physical components. These physical components may comprise hard-wired (such as a computer specially constructed for the desired purposes) or programmable devices (such as general-purpose computer specially configured for the desired purpose), or a combination of the two. In some embodiments, at least some of the functions of the processing circuitry may be carried out by a programmable processor under the control of suitable software. This software may be downloaded to a device in electronic form, over a network, for example. Alternatively or additionally, the software may be stored in tangible, non-transitory computer-readable storage media, such as optical, magnetic, or electronic memory. The term "non-transitory" is used herein to exclude transitory, propagating signals, but to otherwise include any volatile or non-volatile computer memory technology suitable to the application.

It is appreciated that software components of the present disclosure may, if desired, be implemented in ROM (read only memory) form. The software components may, generally, be implemented in hardware, if desired, using conventional techniques. It is further appreciated that the software components may be instantiated, for example: as a computer program product or on a tangible medium. In some cases, it may be possible to instantiate the software components as a signal interpretable by an appropriate computer, although such an instantiation may be excluded in certain embodiments of the present disclosure.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

Figure 1B:
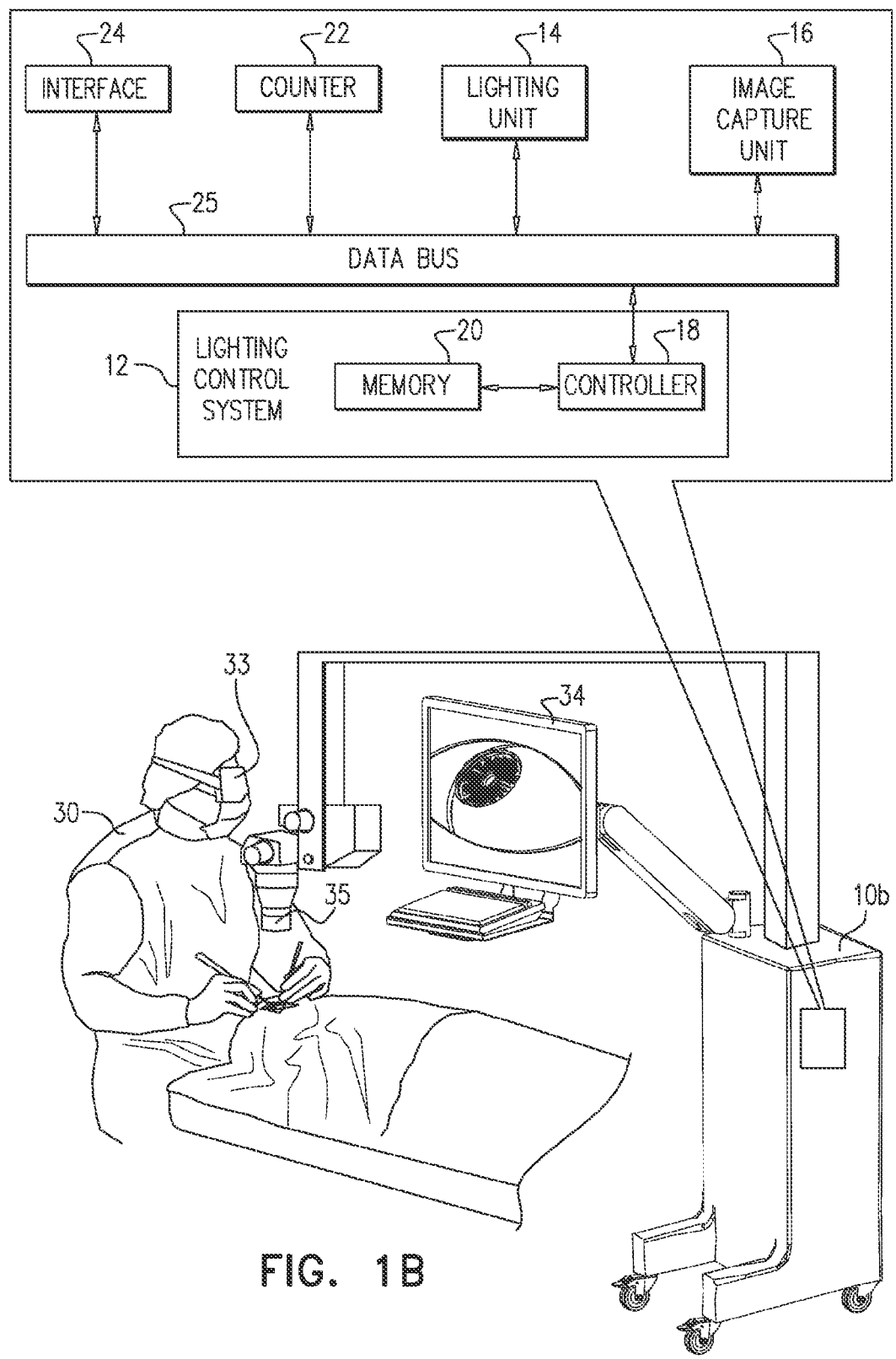

In embodiments of the presently disclosed subject matter, fewer, more and/or different stages than those shown in FIGS. 2, 3, 4, 5, 9 and 10 may be executed. In embodiments of the presently disclosed subject matter one or more stages illustrated in FIGS. 2, 3, 4, 5, 9 and 10 may be executed in a different order and/or one or more groups of stages may be executed simultaneously. FIGS. 1*a* and 1*b* illustrates a general schematic of the system architecture according to an embodiment of the presently disclosed subject matter. Each module in FIGS. 1*a* and 1*b* may be made up of any combination of software, hardware and/or firmware that performs the functions as defined and explained herein. The modules in FIGS. 1*a* and 1*b* may be centralized in one location or dispersed over more than one location. In other embodiments of the presently disclosed subject matter, the system may comprise fewer, more, and/or different modules than those shown in FIGS. 1*a* and 1*b*.

It is to be noted that, with reference to each of the flowcharts of FIGS. 2, 3, 4, 5, 9 and 10, some of the blocks can be integrated into a consolidated block or can be broken down to a few blocks and/or other blocks may be added. Furthermore, in some cases, the blocks can be performed in a different order than described herein. It is to be further noted that some of the blocks are optional. It should be also noted that whilst the flowchart is described also with reference to the system elements that realizes them, this is by no means binding, and the blocks can be performed by elements other than those described herein.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Bearing this in mind, reference is now made to FIGS. 1*a* and 1*b*, which are a partly pictorial, partly block diagram views of a surgical microscope systems 10*a* and 10*b* respectively, both collectively referred to herein as "surgical microscope system 10", constructed and operative according to embodiments of the present disclosure.

Most eye procedures are short and last less than an hour or even half an hour. Nevertheless, illumination levels are high, and the phototoxicity damage to the eye is accumulative and can become substantial even in those short intervals of time. Additionally, exposure to illumination may be extremely uncomfortable for a patient. The surgical microscope system 10 is configured to automatically determine in real-time whether the illumination is actually required, and reduce the damaging and discomforting light in the short time intervals when it is not. The potential reduction using the surgical microscope system 10 may be small, but even small reductions are significant.

It should be noted that when reference is made to illumination herein, it is to illumination controlled by the surgical microscope system 10 only. Various types of eye surgery also involve using fiber light, which is often controlled by a separate system. It is to be noted that although reference is made herein to illumination controlled by the surgical microscope system 10 only, the presently disclosed subject matter is also applicable to controlling illumination originating from other devices that support external control, including, but not limited to, fiber illumination, mutatis mutandis. Such controlling of other types of illumination during any type of surgery that includes illuminating a surgical site is within the scope of the presently disclosed subject matter.

The surgical microscope system 10, as will be described in more detail below, is configured to reduce the potential hazard of light to the eye, with emphasis on phototoxicity hazard to the retina, caused by light that passes through the pupil. Some of the embodiments described herein may also be useful in medical applications other than eye related applications. The thermal effect of illumination may be harmful and operative microscopes have the ability to cause patient morbidity and in extreme cases even skin burn injuries. In some cases, burn injuries have been reported because of xenon microscope lighting, and burn injuries are generally more frequent during neurosurgical or otolaryngology procedures. Few studies have recommended that surgeons be aware of the issue and minimize illumination intensity and operative time.

The surgical microscope system 10 is configured to automatically identify the time periods when harmful illumination can be reduced or completely blocked, and automatically reduce or block the illumination. For example, the illumination of a body part or a part of the body part may be reduced or blocked during periods of time when it is determined or estimated that the surgeon does not need the light, such as when the surgeon chooses to view preoperative imaging data via a display instead of the magnified image of the surgical field, or during periods of time when no motion is detected in the surgical field and/or no surgical tools are present within the surgical field, or during stages of a surgical workflow in which illumination through the pupil, or white light, or illumination in general is not required. By way of another example, when the head-mounted display of the surgeon is pointing away from the general direction of the region of illumination and no motion is detected (e.g., by cameras) in the surgical field (being, during most of the procedure, but not necessarily throughout the entire procedure, the region of illumination), illumination may be reduced or stopped. However, if motion is detected in the region of illumination while the head-mounted display of the surgeon is pointing away from the general direction of the region of illumination, the surgeon may be assumed to be looking to the side while at the same time the nurse may be, for instance, applying eye-drops to the patient's eye and needs the illumination in the surgical field. Other examples are described in more detail below with reference to FIGS. 2-5.

Reducing damaging illumination may be based on dynamically blocking only the light that illuminates the retina or any other sensitive body part (e.g., a part of the brain), in those periods of time when illumination is not required for the surgical procedures. Alternatively, reducing the damaging illumination can be based on switching between illuminating with white light, i.e. light that comprises energy in the entire visible wavelength, and light that does not comprise energy in a harmful spectrum (e.g. light in a blue spectrum is considered more harmful for the retina), or simply reducing the level of white light illumination. Blocking or reducing illumination is described in more detail with reference to FIGS. 6 and 7 below.

The surgical microscope system 10, in addition to being configured to automatically identify the time periods when harmful illumination can be reduced or completely blocked, is also configured to automatically adjust the illumination level for optimizing the surgical workflow and freeing the surgeon from the need to manually adjust the illumination level many times during the procedure. This need arises from the fact that different stages of a surgical procedure require different intensities and different types of illuminations. For example, by estimating the current stage of the surgery, and based upon predetermined levels of illumination suitable for each stage, the surgical microscope system 10 can determine the required levels of flood and/or coaxial illumination and automatically adjust the illumination levels (coaxial illumination is illumination in which light from a light source is diverted by a semi-transparent mirror so it is projected along an optical axis of a viewer or a camera. In some ophthalmic procedures coaxial illumination is used so the user sees light reflected from the retina which allows better visualization of parts of the anterior segment of the eye). Other examples are described in more detail below, e.g. with reference to FIGS. 2-5.

The surgical microscope system 10 includes a lighting control system 12, a lighting unit 14, an image capture unit 16, and a data bus 25. The lighting unit 14 and the image capture unit 16 can be comprised within a camera-head unit 35 suspended above the surgical field. The lighting control system 12 includes a controller 18 and optionally a memory 20. The memory is configured to store data used by the controller 18. The surgical microscope system 10 may optionally include a counter 22 and an interface 24. The lighting control system 12 controls an illumination provided by the lighting unit 14. The lighting control system 12 is described in more detail with reference to FIGS. 2-9. The image capture unit 16 may include optical and/or electronic components to capture images in a field of view. It is to be noted, in this respect, that the live magnified video generated by the image capture unit 16 may be used for the methods described here, for recording the procedure, and for displaying it, e.g. via monitor 34, for the benefit of the staff in the operating room. In addition, the live magnified video may be viewed by the surgeon, e.g. via monitor 34 or via HMD 32. Alternatively, the surgeon may view a non-digital magnified view of the surgical field via an eyepiece or eyepieces, when they are included in surgical microscope system 10. When the surgical microscope system 10 is fully digital the surgeon may not have a non-digital magnified view of the surgical field via an eyepiece, and in some cases the surgical microscope system 10 does not include any eyepiece at all. The counter 22 is configured to count radiation incident upon a body part and is described in more detail below with reference to FIGS. 8 and 9. The interface 24 is configured to transfer data between the surgical microscope system 10 and external surgical tools, external displays and/or data systems, for example, but not limited to, a medical data system (not shown) including medical histories of patients.

FIG. 1a shows a surgeon 30 wearing a head-mounted display 32 which is connected to the surgical microscope system 10. The head-mounted display 32 may be connected to the surgical microscope system 10 via a wired or wireless connection. The head-mounted display 32 displays video generated by the surgical microscope system 10 comprising image data and other data (such as overlaid symbols, menus, numerical data, textual data, etc.) generated by the surgical microscope system 10 itself and optionally additional data (in an image form or in any other form, including text, etc.) received by surgical microscope system 10 from other external systems, such as the medical data system, a phacoemulsification machine, an endoscope camera, etc. The additional data can be pre-acquired data, or data acquired or generated in real-time by one or more of the other external systems. The image data includes images captured by the image capture unit 16 and optionally other medical data relating to the patient. The images captured by the image capture unit 16 may be displayed via an external display 34 (e.g., a 2D or 3D monitor). The data bus 25 is configured to connect the various elements of the surgical microscope system 10 for data transfer purposes.

FIG. 1b shows the surgeon 30 wearing three-dimensional glasses 33 which enable viewing three-dimensional images presented on the external display 34 (which, in this embodiment, is a 3D monitor). The external display 34 may display a video generated by the surgical microscope system 10 comprising image data and other data (such as overlaid symbols, menus, numerical data, textual data, etc.) generated by the surgical microscope system 10 itself and optionally additional data (in an image form or in any other form, including text, etc.) received by surgical microscope system 10 from other external systems, such as the medical data system, a phacoemulsification machine, an endoscope camera, etc. As indicated above, the additional data can be pre-acquired data, or data acquired or generated in real-time by one or more of the other external systems. The image data includes images captured by the image capture unit 16 and optionally other medical data relating to the patient. The data bus 25 is configured to connect the various elements of the surgical microscope system 10 for data transfer purposes.

It is to be noted, with reference to FIGS. 1a and/or 1b, that in some embodiments, the surgical microscope system 10 can include eyepiece(s) (not shown) through which a magnification of the surgical field can be viewed. In such cases, the surgeon 30 may choose not to use, or may not be equipped with, the head-mounted display 32 and/or the three-dimensional glasses 33 and/or the external display 34. When eyepiece(s) are provided, the surgical microscope system 10 may also include a proximity sensor to sense a proximity of the surgeon 30 to the eyepiece(s). The function of the proximity sensor is described in more detail with reference to FIGS. 4 and 10 below.

Figure 2:
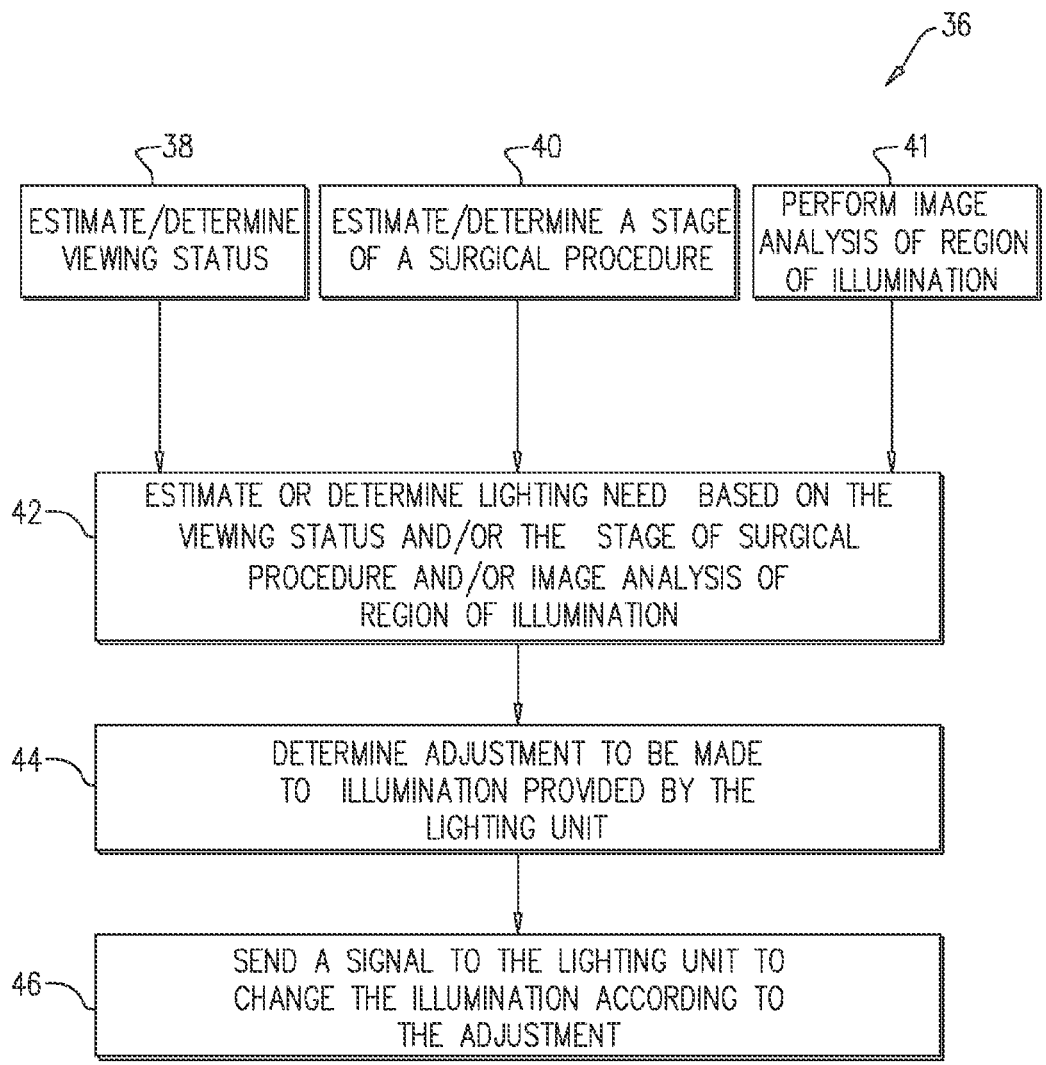
FIG. 2 is a flowchart including exemplary steps in a method of controlling illumination in the surgical microscope system of FIGS. 1a and 1b.

Reference is now made to FIG. 2, which is a flowchart 36 including exemplary steps in a method of controlling illumination in the surgical microscope system 10 of FIGS. 1a and 1b. Reference is also made to FIGS. 1a and 1b. The controller 18 is configured to estimate or determine (block 38) a viewing status of a region of illumination by the surgeon 30. Alternatively, or additionally, the controller 18 is configured to estimate or determine (block 40) a stage of a surgical procedure. Alternatively, or additionally, the controller 18 is configured to perform (block 41) an image analysis related to the region of illumination viewed by at least one sensor (e.g., camera or other imaging device). In some embodiments the outputs of block 38 relating to the viewing status and/or the outputs of block 41 relating to the image analysis are used to estimate or determine the stage of the surgical procedure of block 40. Similarly, in some embodiments the outputs of block 41 relating to the image analysis are used to estimate or determine the viewing status of block 38. Examples of such combinations are included below. It will be appreciated that any suitable combination and/or permutation of the processes of blocks 38, 40 and/or 41 may be implemented.

The controller 18 is configured to estimate or determine (block 42) a lighting need of the surgeon 30 during at least part of the surgical procedure based at least on any one or two or more of the following: (a) the viewing status of the region of illumination by the surgeon 30; (b) the stage of the surgical procedure and a plurality of predetermined lighting needs at a plurality of stages of the surgical procedure;

and/or (c) an image analysis related to the region of illumination viewed by at least one sensor.

So, for example, if the lighting need is based on the viewing status of the region of illumination by the surgeon 30, if it is determined or estimated that the surgeon 30 is not looking at the region of illumination, the lighting need may be low or non-existent.

By way of another example, if the lighting need is based on the stage of the surgical procedure, and assuming that a given stage of a given surgical procedure includes removing the surgical microscope system 10 away from the patient's eye and using the surgical microscope system 10 to prepare an intraocular lens for inserting during cataract surgery, the lighting need of such given stage may be in accordance with a predetermined lighting need associated with this stage.

Determination and/or estimation of the lighting need of the surgeon 30 during at least part of the surgical procedure using image analysis is described in more detail with reference to FIG. 3. Determination and/or estimation of the viewing status is described in more detail with reference to FIG. 4. Determination and/or estimation of the stage of the surgical procedure is described in more detail with reference to FIG. 5.

It is to be noted that in some cases, the lighting need estimation can be accompanied by a calculated confidence score, indicative of a confidence level of the estimation.

The controller 18 is configured to determine (block 44) an adjustment to be made to the illumination provided by the lighting unit 14 based on the lighting need. The adjustment may include changing an intensity of the illumination, for example using any one or more of the following: stopping the illumination; adjusting the level of a power source or a current source driving the illumination; adjusting an optical element disposed in the optical path of the lighting unit to change the size of the spot of light; modifying the temporal pattern of the illumination; electrically controlling a permanent liquid crystal shutter disposed in an optical path of the lighting unit; disposing a beam splitter into the optical path or removing it; disposing a digital mirror device into the optical path or removing it; disposing a neutral-density filter into the optical path or removing it, or any suitable combination thereof. The adjustment can additionally or alternatively include changing a spectrum of radiation of the illumination provided by the lighting unit. Changing a spectrum can be performed for example using a filter wheel placed in the optical path of the lighting unit. The adjustment is described in more detail with reference to FIGS. 6 and 7. The controller 18 is configured, in response to determining the adjustment, to send (block 46) a signal to the lighting unit 14 to change the illumination according to the adjustment.

In case the lighting need estimation is accompanied by a calculated confidence score, the confidence score can also be used in the determination of the adjustment. For example, if the confidence score is high (or even full confidence when the lighting need is determined and not estimated), then the adjustment is made accordingly, whereas if the confidence score is low, the adjustment may be determined to be different than the determined estimated lighting need.

Figure 3:
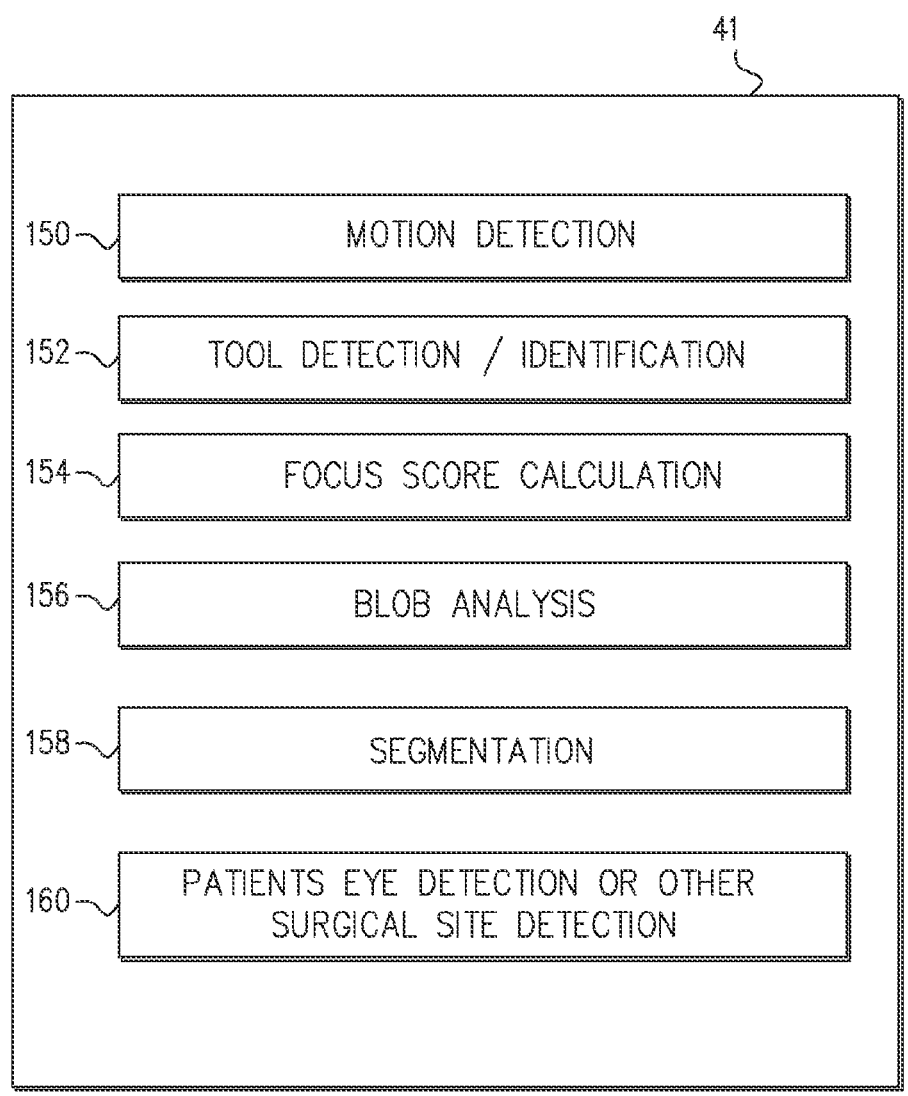
FIG. 3 is a more detailed view of the perform image analysis of a region of illumination step.

Reference is now made to FIG. 3, which is a more detailed view of the perform image analysis of a region of illumination step of block 41 of FIG. 2. Reference is also made to FIGS. 1*a* and 1*b*. The image analysis may be used for estimating or determining a lighting need in a variety of ways which may be used independently, or in any suitable combination, to estimate or determine the lighting need. It will be appreciated that other ways for estimating or determining the lighting need may also be used to implement the surgical microscope system 10.

The estimation/determination of the lighting need using image analysis may be based on any one or more of the following inputs, by way of example only: video from cameras generating or capturing a magnified image; video from other cameras (e.g., an infrared (IR) camera for motion detection with IR illumination); and/or image data from modules that generate an image like an intraoperative optical coherence tomography (OCT). It should be noted that the surgeon 30 may be watching a small region-of-interest (ROI) within an entire captured frame, but image analysis generally may have access to the entire captured frame. It should be noted that the various cameras and imaging devices may be capturing different size regions or the same size regions.

Outputs from the image analysis functions may include specific scores/results, and optionally corresponding confidence scores, calculated by any one or more of the following modules or methods: motion detection, histogram data analysis, tool detection and/or identification, a focus score calculation, blob analysis, segmentation, and/or detection of a patient's eye or other surgical sites to detect whether the surgical field is in the image or not. It will be appreciated that other image analysis functions/modules may be used, and the above are only brought by way of example only. Some of the image analysis functions are described in more detail below with reference to FIG. 4 and FIG. 5 where image analysis functions may also be used as part of determining and/or estimating the viewing status and/or the stage of the surgical procedure.

It should be noted that the outputs may include time stamps so that timings and durations may be used in estimating or determining the lighting need of the surgeon 30. For example, in estimating or determining the lighting need of the surgeon 30, if it may be determined that the head-mounted display 32 is pointing away from the region of illumination and additionally there is no motion in the region of illumination for five consecutive seconds, then it may be estimated that lighting is not required.

The following is an example of using motion detection for determining a lighting need of the surgeon 30. For this purpose, the controller 18 may be configured to detect motion in the region of illumination (block 150). Lack of motion for more than a given time period (e.g., 5 seconds) may indicate that illumination may be reduced. It is to be noted that in order to be able to perform motion detection, or any other type of image analysis, a certain amount of light is required. Therefore, in some cases, at least some level or type of illumination is provided when capturing images that are later analyzed by the presently disclosed system. It is to be further noted that the camera used for motion detection may be an IR camera that may also have a dedicated IR illumination, and may cover a region of interest that is larger than the visible-light region of illumination. This may allow the surgical microscope system 10 to detect motion, e.g. a tool about to enter the visible-light region of illumination, before it actually enters the region of interest that is seen by the surgeon, and adjust the illumination without delay. It is to be noted that although reference is made herein to motion detection using image analysis, motion detection can be performed using also other types of motion detection sensors know in the art.

The following is an example of using tool detection and/or identification for determining a lighting need of the surgeon 30. For this purpose, the controller 18 may be configured to detect a presence or an absence of surgical tools in, and generally around, the region of illumination (block 152). Disappearance of surgical tools from, and from generally around, the region of illumination, may indicate that illumination may be changed (e.g. reduced). Re-appearance of a surgical tool in, and generally around, the region of illumination, may indicate that the illumination should be again changed (e.g. returned to the previous state prior to disappearance of the surgical tool). As long as surgical tools are present in, and generally around, the region of illumination, it may indicate that illumination should be kept unchanged.

However, in some cases, in response to finding a tool(s) in, and generally around, the region of illumination, the controller 18 may be configured to reduce the illumination in, and optionally around, the region of illumination or modify a spatial pattern of the illumination to reduce or remove illumination in a region of the tool(s) to reduce saturation of the image based on glare produced by the tool(s). Modifying a spatial pattern is described in more detail with reference to FIGS. 6 and 7.

The following is an example of using a focus score (optionally in conjunction with motion detection and tool detection) in the image analysis processing for determining a lighting need of the surgeon 30. For this purpose, the controller 18 may be configured to calculate a focus score indicating whether or not the region of illumination is in focus (block 154). It should be noted that for this example it is assumed that the surgical microscope system 10 does not support an auto-focus function, or that the auto-focus function is disabled (i.e. focus is manually adjusted by the surgeon). In the example, the surgeon 30 moves the microscope system 10 away from the surgical field but still over the patient's body. The surgeon 30 takes off the head-mounted display 32 and the image is not in focus for a long time. The illumination may generate a burn on the patient's skin. It should be noted that there may still be movement in the image if the actions of the surgeon 30 outside the region of illumination are moving the patient. A determination that the surgeon 30 is not wearing the head-mounted display 32 in addition to a determination of a low confidence that relevant motion is performed within the images (e.g., if there is motion in the images, but nothing that resembles a tool in the image, then the motion detection confidence may be low as the motion is less likely relevant) in addition to no focus may indicate that lighting is not required.

Predefined time thresholds may be used in relation to adjusting the illumination. For instance, the controller 18 may be configured so that no motion is detected for more than a given time period (e.g., 5 seconds) before illumination is reduced. By way of another example, the controller 18 may immediately reduce illumination (zero seconds waiting period) if the surgeon 30 chooses to view preoperative data via the head-mounted display 32. In general, any combination of scenarios may have its own predefined time thresholds after which the illumination may be adjusted. Moreover, different levels of algorithmic confidence regarding the estimated viewing status or stage or any of the image analysis functions may have different time thresholds. For instance, in the skin burn example given above, the controller 18 may be configured so that non-viewing in addition to a low confidence of motion, in addition to no focus, may be associated with a given waiting period (e.g., one-minute waiting period) before reducing illumination.

The following is an example of using blob analysis for determining a lighting need of the surgeon 30. For this purpose, the controller 18 may be configured to perform blob analysis (block 156) (blobs are connected regions in the image having similar properties). Blob analysis may be implemented to detect saturated areas in the image. Reflection of the illumination from a patient's eye may generate a detectable pattern of small blobs, and therefore the existence of such a pattern may be used for detecting an eye in the image (or more specifically an external part of an eye, as opposed to an internal part thereof). In general, blobs that have shapes and/or sizes that meet certain rules (e.g. their number of pixels is larger than a threshold), or existence of a number of blobs above a threshold, or existence of a certain pattern of blobs, or a certain blob dynamics over a plurality of frames (e.g. a certain blob size increases or a blob moves), or location of a blob, may be used in various ways, such as for detecting a patient's eye, for detecting tools in general or specific tools, for detecting motion in the illuminated region, and for determining a stage in the procedure.

For example, detection of a blob having identifiable shape and size (i.e. the height of the microscope above the eye is always the same, hence the size of a tool in the image will always be similar) at the bottom of an analyzed image and detection of movement thereof at subsequently analyzed images (i.e. blob dynamics over consecutive frames) towards the edge of the cornea (which is identified for instance by segmentation) may indicate a stage in the procedure in which the surgeon is performing a wide cut in the cornea. This stage may require that the illumination is best fitted for the region of the cut, even if on the expense of less-than-optimal illumination at other regions in the image. For instance, the illumination may be reduced to avoid saturation due to reflections from the flat tool the surgeon is using, although this might cause other regions in the image to appear dark. The end of this stage may be indicated by the disappearance of the tool. It is to be noted that each surgeon may operate differently (e.g. an operation conducted by a first surgeon may include stages that are not performed, or are performed differently, by another surgeon), use different tools, etc., and these may be learned so the stage-determination may be personalized.

The following is an example of using segmentation for determining a lighting need of the surgeon 30. For this purpose, the controller 18 may be configured to perform segmentation analysis (block 158). Segmentation can be used to partition an analyzed image into separate entities (e.g. based on grey level and/or color and/or texture and/or shape, etc.)—pupil, iris, blood vessel, tool, finger, etc. It may be used for example for detecting an eye in the image. Additionally, when segments with the expected shapes and sizes of a pupil and iris are detected but blood vessels are not detected, it may indicate that the illumination is too high or too low. Furthermore, sequential segmentation results (obtained for example by performing segmentation analysis of a sequence of consecutively acquired images) may be used to estimate movement of a tool within the region of illumination.

The following is an example of using patient's eye detection or another surgical site detection for determining a lighting need of the surgeon 30. For this purpose, the controller 18 may be configured to perform patient's eye detection or another surgical site detection (block 160). Any appearance or disappearance (i.e. change in the detection status) of the patient's eye or another surgical site in the region of illumination may indicate that the lighting need changed. For instance, if the eye disappeared and a tool appeared it might indicate that the illumination should be decreased, and if the eye reappeared then it might indicate that the illumination should be increased.

Figure 4:
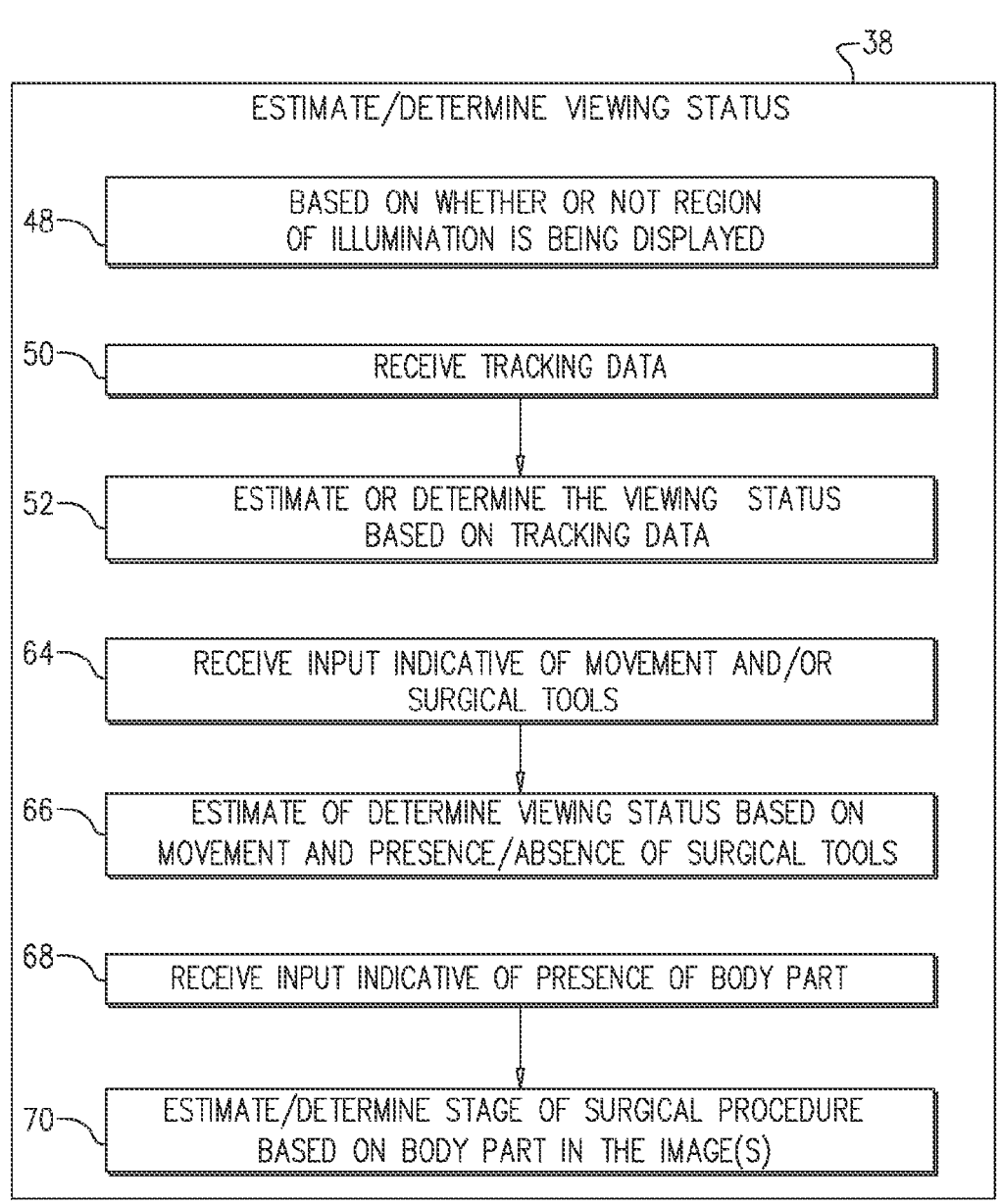
FIG. 4 is a more detailed view of the estimate/determine the viewing status step included in the flowchart of FIG. 2.

Reference is now made to FIG. 4, which is a more detailed view of the estimate/determine the viewing status step of block 38 of FIG. 2. Reference is also made to FIGS. 1a and 1b. The viewing status may be estimated or determined in a variety of ways which may be used independently, or in any suitable combination, to estimate or determine the viewing status. It will be appreciated that other ways for estimating or determining the viewing status may also be used to implement the surgical microscope system 10.

The estimation/determination of the viewing status may be based on any one or more of the following inputs, by way of example only: what the surgeon 30 decides to see via the head-mounted display 32; tracking the orientation and/or the position of the head-mounted display 32 including using a flag for standby indicating when the head-mounted display 32 is not in use; eye-gaze tracking (e.g., via the head-mounted display 32); head and eye tracking via other sensors (e.g., when the head-mounted display 32 is not included in the system 10); and/or data from a proximity sensor which indicates whether someone (e.g., the surgeon 30) is in proximity to an eyepiece(s) through which image data originating from the surgical microscope system 10 can be viewed. The estimation/determination of the viewing status may provide one or more of the following outputs, by way of example only: a probability (e.g., confidence score) that the surgeon 30 is watching the region of illumination (either directly or indirectly); selective data from the inputs, such as position and orientation data, and eye-gaze direction. It should be noted that the outputs may include time stamps so that timings and durations may be used in estimating or determining the lighting need of the surgeon 30. For example, in estimating or determining the lighting need of the surgeon 30, if it may be determined that the head-mounted display 32 is pointing away from the region of illumination and additionally there is no motion in the region of illumination for five consecutive seconds, then a decision may be determined to decrease illumination.

One indication of the viewing status is whether or not the surgeon 30 is watching a screen that includes a live magnified video of the region of illumination. It should be noted that the surgeon 30 may be watching a screen displaying preoperative data that also includes a picture-in-picture (PIP) displaying the live magnified video of the region of illumination. If the surgeon 30 is donning the head-mounted display 32 (which may be indicated by movement of the head-mounted display 32) the viewing status may be estimated or determined by what is being displayed by the head-mounted display 32. If the surgeon 30 is not donning the head-mounted display 32, the surgeon may be viewing the live magnified image via the external display 34 and the viewing status may be estimated or determined by what is being displayed by the external display 34. Therefore, the controller 18 may be configured to estimate or determine the viewing status of the region of illumination based at least on whether or not the region of illumination is being displayed (block 48).

Alternatively, or additionally, the controller 18 may be configured to analyze head or other movements of the surgeon 30 and/or movements of the head-mounted display 32 based on tracker data to determine the viewing status of the magnified image. For example, during rapid head movements or when looking sideways, the controller 18 may assume that the surgeon 30 is not concentrating on the magnified image. Another example is when the surgeon is not donning the head-mounted display 32 which may be detected by lack of movement of the head-mounted display 32 as tracked by a tracker system. It should be noted that during both initial and final stages of the surgical procedure, the surgeon 30 may prefer not to don the head-mounted display 32 since a magnified image may not be used at these stages, yet the illumination is still needed by the surgeon 30. In such a case, motion detected in the region of illumination may indicate that the illumination should be kept unchanged. The tracker system may also detect that the surgeon 30 has stepped away from the region of illumination. The tracker may be based on an optical tracker and or inertial sensors, e.g., accelerometers, or any other suitable tracker.

Alternatively, or additionally, the viewing status may be determined based on given positional or angular boundaries of the head-mounted display 32 outside of which illumination is not required at all or at the current level. The positional and angular boundaries may be user-defined (e.g. surgeon-specific).

Therefore, the controller 18 may be configured to: receive (block 50) tracking data of the surgeon 30 or the head-mounted display 32; and estimate or determine (block 52) the viewing status of the region of illumination based at least on the tracking data. The tracking data may include any one or more of the following: a position of a head of the surgeon 30 and/or the head-mounted display 32; a rate of movement of the head and/or the head-mounted display 32; an orientation of the head and/or the head-mounted display 32; and/or eye gaze data. It should be noted that the system 10 may support multiple users (e.g., 2 or 3 users) and any one of these users may be watching the video of the live magnified image. It should also be noted that other people in the operating room, e.g., a nurse, may be tracked.

The tracking data may indicate that the region of illumination is not being viewed by the surgeon 30 when the tracking data indicates any one or more of the following: head movements greater than a given rate; the surgeon 30 is looking outside (i.e., is not looking in the general direction) of the region of illumination or outside of given angular boundaries (it should be noted that when using a head-mounted display the surgeon may still see the region of illumination and attend to it while pointing the head away from the surgical site. However, when the surgeon is turning the head away from the illuminated region by more than a given threshold it may be assumed that the surgeon is not attending the surgical site); the head-mounted display 32 is not moving as it is not being worn; the head-mounted display 32 is stowed; the surgeon 30 is peeking around the head-mounted display 32 away from the region of illumination; and the surgeon 30 has stepped away from a given region where the surgical procedure is taking place. The tracking data may indicate that the region of illumination is being viewed by the surgeon 30 when the tracking data indicates any one or more of the following: the surgeon 30 is looking towards the region of illumination or inside of the given angular boundaries when the head-mounted display 32 is transparent or in a transparent state (i.e. when the head mounted display can switch between a transparent state as in augmented-reality head mounted systems and an opaque state as in virtual-reality head mounted systems); the surgeon 30 is peeking around the head-mounted display 32 but towards the region of illumination; and the head-mounted display 32 is stowed or is not being worn, but the surgeon 30 is looking at the region of illumination (which may be determined based on an external camera tracking the head of the surgeon 30 or by any other suitable method).

The controller 18 may be configured to: use eye gaze data of the surgeon 30, comprised within the tracking data, indicating where the surgeon is looking within the magnified video of the patient's eye or other body part that is displayed via the head-mounted display 32 (and optionally additional data such as the location of various identified segments in the image, as received from the image analysis block, which enables translating the information of where the surgeon 30 is looking at within the displayed image to a part of the patient's eye that is located at the observed coordinates), and to estimate or determine how to adjust a current illumination provided by the lighting unit. For example, the surgeon 30 may be looking at the eye sclera (which may be determined by identifying the coordinates that the surgeon 30 is looking at and determining that they are within the eye sclera, e.g. using image analysis to identify the specific part of the eye that is located at the observed coordinates). In such a case, the illumination provided through the pupil may be stopped or reduced or changed to a different, less damaging, type of light color, for example, but not limited to, IR illumination.

In addition, the eye gaze data can be used to determine where the surgeon 30 is looking also in cases where the surgeon 30 is not looking at the images displayed on the head-mounted display 32, but peeking outside of the head-mounted display 32. When eye-gaze tracking is implemented via sensors in the head-mounted display 32, the peeking direction is relative to the head-mounted display 32. Since the head-mounted display 32 movements are also tracked, the peeking direction relative to the illuminated region can be determined. For example, the surgeon 30 may be peeking outside the head-mounted display 32, and not at the illuminated region. In such a case, the illumination may be changed (e.g. stopped or reduced).

It is to be noted, for example, that if the system 10 comprises eye-gaze tracking, and an eye-gaze subsystem indicates that the surgeon 30 is focusing on a local saturated part of the magnified image (e.g. found during image analysis), then the system 10 may eliminate the saturation by reducing the illumination globally or locally (using spatial modulation described in more detail below with reference to FIGS. 6 and 7). If the system 10 does not comprise eye-gaze tracking, the image analysis process may further identify a shape in the image as a tool and the system 10 may estimate that the surgeon 30 is focusing on that tool. Alternatively, the system 10 may estimate that when a small area is saturated in a certain stage of the surgical procedure then the illumination may be reduced.

In some cases, the tracking data can include proximity data obtained by a proximity sensor. For example, if the surgical microscope system 10 includes an eyepiece(s) through which the magnified illuminated region can be viewed and a proximity sensor which indicates whether someone (e.g., the surgeon 30) is in proximity to the eyepiece(s), it will be appreciated that a viewing status may be indicated based on whether or not someone (e.g., the surgeon 30) is in proximity to the eyepiece(s). The proximity sensor may be implemented as a camera which detects the head of the surgeon 30 or any other suitable proximity sensor such as a touch sensitive sensor or time-of-flight sensor by way of example only. Therefore, the controller 18 may be configured to: estimate or determine the viewing status of the region of illumination based at least on the proximity data, providing an indication of whether or not the surgeon 30 is in proximity to the eyepiece(s) of the surgical microscope system 10.

The viewing status of the region of illumination by the surgeon 30 may be indicated by at least movement in, or generally around, the region of illumination or the presence/absence of tools in, and generally around, the region of illumination. Movement is typically determined based on results of image analysis processing. The image analysis processing may comprise any suitable method or methods, for example, but not limited to, using motion detection algorithm as a part of the image analysis along with one or more other image processing techniques.

It will be appreciated that the viewing status may be based on any suitable combination of factors described herein. The movement or the tools may be detected based on image analysis of the magnified image. When no movement and/or no tools are detected, the illumination may be reduced or stopped. When a tool or movement is again detected in, and generally around, the region of illumination, the illumination may be increased. Therefore, the controller 18 is configured to: receive input (block 64) indicative of movement and/or surgical tools at least at the region of illumination; and estimate or determine (block 66) the viewing status of the region of illumination based at least on the movement, and/or a presence or an absence of the surgical tools in at least the region of illumination. It should be noted that the movement detection is not restricted to the region of illumination, but may also include an area around the region of illumination. Motion/movement detection and tool detection may be performed based on a low-resolution video taken by a camera either disposed in or adjacent to the surgical microscope system 10, or based on video taken by microscope system 10 itself.

It should be noted that very high-resolution cameras may be used for imaging a relatively large field of view (FOV), and the user or surgeon 30 may choose to zoom in to see only a small part of the FOV (hence the FOV image is magnified). Although the surgeon 30 sees a part of the FOV, the entire FOV is still generally imaged. Motion detection may be based on the full image (either the original image or a binned image (an image having a smaller resolution than the full image but covering the entire FOV derived from the original image). It should also be noted that motion detection may be based on video from one of the microscope cameras or even based on video from more than one camera as previously mentioned above.

Employing motion and/or tool detection generally uses some sort of illumination in, and generally around, the region of illumination. Therefore, completely shutting down the illumination in periods when no motion or tools are detected is generally not appropriate. A lower level or pulsed illumination may be used. Alternatively, IR illumination may be used for motion detection instead of using white light illumination. It should be noted that if a camera that is used for generating the magnified image (and is focused for white light) is also used for motion detection with IR light, then the IR video might be out of focus (depending on the camera optics), but motion detection may generally still be performed.

Similarly, the controller 18 may be configured to: receive input (block 68) indicative of whether a body part that is being operated on is included in the image(s); and estimate or determine (block 70) the viewing status based at least on whether the body part is included in the image(s).

It should be noted that tool detection and other image analysis functions may also be used to estimate the stage of the surgical procedure. Therefore image analysis, in addition, or alternatively, to providing a direct estimation or determination method of the illumination needs of the surgeon 30, and in addition, or alternatively, to providing input to estimate or determine the viewing status, also provides an input to estimating or determining the stage of the surgical procedure. If the stage estimation/determination is implemented using machine learning, image analysis may be used during both the learning phase and the operation phase. Additionally, or alternatively, data used and/or outputted in determining/estimating the viewing status may be used to estimate the stage of the surgical procedure.

Figure 5:
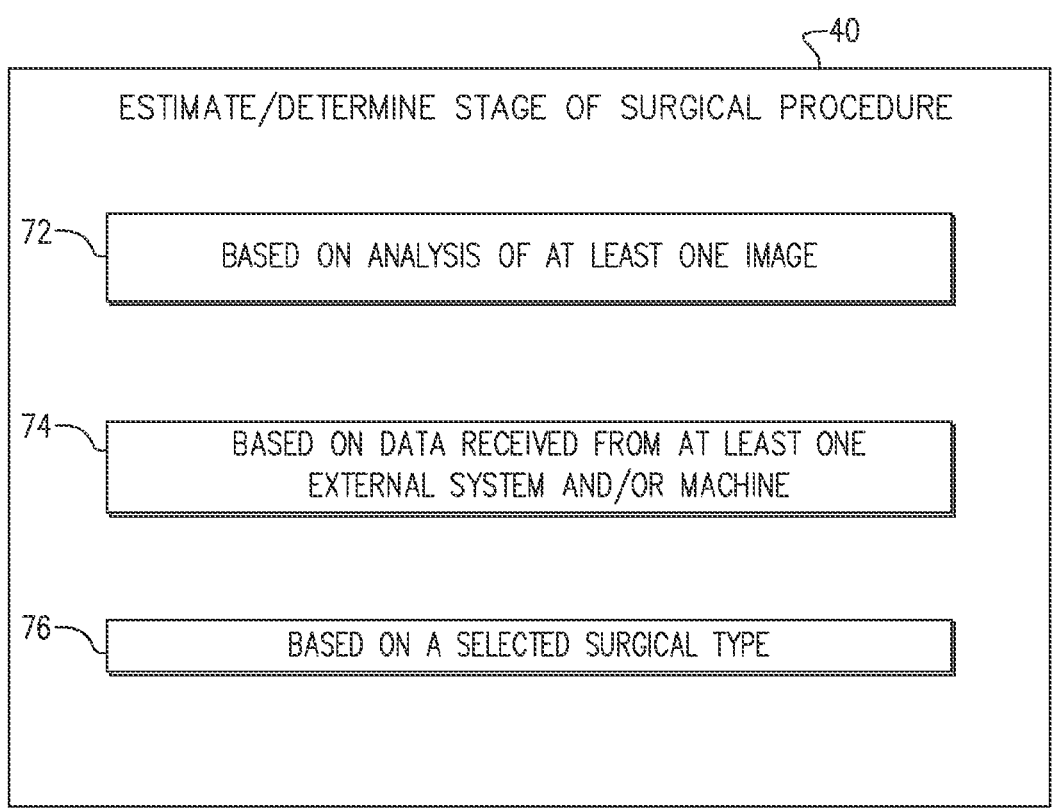
FIG. 5 is a more detailed view of the estimate/determine the stage of surgical procedure step included in the flowchart of FIG. 2.

Reference is now made to FIG. 5, which is a more detailed view of the estimate/determine the stage of surgical procedure step of block 40 of FIG. 2. Reference is also made to FIGS. 1a and 1b.

In eye surgery, by way of example, there are stages during surgery when the surgeon is focused on surgical locations in which illumination through the pupil is not required. Examples for such periods are when the surgeon places trocars in the eye sclera at the beginning of a vitreoretinal surgery, and when the surgeon removes the trocars and stitches the sclera at the final stages of the surgery.

By way of another example, in vitreoretinal surgery the majority of the procedure is performed with fiber illumination that is not controlled by the surgical microscope system 10, and the surgical microscope system's 10 illumination is turned off. The controller 18 can be configured to identify the stage of the procedure as a posterior-eye stage based on various indication/s (e.g. the user switches to posterior-eye mode, the automatic detection of lowering an arm holding a noncontact lens by the surgeon, and/or other system characteristics are changed in a manner that is specific for a posterior-eye procedure) and turn off the illumination automatically.

By way of another example, in anterior-segment procedures various stages of the procedure require coaxial illumination for generating red reflex from the retina. The controller 18 can be configured to identify the stage of the procedure as a stage requiring coaxial illumination based on various indications, and adjust the flood and coaxial illuminations respectively and per the predetermined settings of the surgeon 30.

It will be appreciated that in other non-eye surgical procedures, such as brain surgery, similar consideration may also be relevant in that certain stages of surgery use a spectrum and intensity of illumination, whereas other stages may use a different spectrum and/or intensity of illumination or no illumination.

The estimation/determination of the stage of surgical procedure may be based on any one or more of the following inputs, by way of example only: a procedure type that was selected via a user interface (e.g., a touchscreen); data from external machines/systems (e.g. a Phaco machine) or the existence of an active connection with given external machines/systems; data indicating movement of a camerahead unit 35; if the camera-head unit 35 or an arm holding it include motors to control focus, x-y movement, etc. then data from at least one controller of the motors; if the camera-head unit 35 is suspended by a robotic arm then data from a controller of the robotic arm; if the camera-head unit 35 is suspended by a manual arm then data from accelerometers in camera-head unit 35; and/or data available in "viewing status" and "image analysis" processes. The output(s) may then be used along with a recommended illumination for each stage (which may be user-specific) in estimating or determining the lighting need of the surgeon 30. It should also be noted that "stage estimation" may be personalized since each surgeon may perform specific stages in a surgical procedure and have different habits during the various stages, therefore estimation/determination of the stage of surgical procedure may also be based on surgeon identity.

The controller 18 can be configured to estimate or determine the stage of the surgical procedure based at least on analysis of at least one image captured by the surgical microscope system 10 (block 72). For example, image analysis can be used to determine whether a body part is included in the image(s), and the stage of the surgical procedure can be estimated or determined based at least on whether the body part is included in the at least one image. By way of another example, image analysis can be used to determine whether a specific tool in the image(s), and the stage of the surgical procedure can be estimated or determined based at least on whether the tool is included in the at least one image.

Alternatively, or additionally, the controller 18 is configured to estimate or determine the stage of the surgical procedure based at least on data received from at least one system or machine disposed externally to the surgical microscope system 10 (block 74).

Alternatively, or additionally, the controller 18 is configured to estimate or determine the stage of the surgical procedure based at least on a selected surgical procedure type (block 76).

Machine learning may be employed to automatically identify the various surgical procedures and the various stages in each procedure in which illumination is, or is not, used by the surgeon 30. The machine learning may even determine how different stages need different illumination levels, or different spectra of illumination and which parts of the body are illuminated (e.g., pupil versus the rest of the eye). This may be performed using supervised and/or unsupervised learning, using time-segmented and tagged video recordings, and/or raw footage in procedures where the surgeon 30 (or other surgeon) manually changes the illumination according to the lighting needs during the surgical procedure, or any other suitable method. The machine learning may be additionally based on one of: raw video data from cameras generating magnified images; raw video from other cameras (e.g. an IR camera having a larger field of view); output of image analysis algorithms performed on that raw video (e.g., algorithms that identify tools in the image; other data such as data from external machines/systems or tools (e.g. a phacoemulsification machine, a phacovitrectomy system, etc.) that are connected to the surgical microscope system 10 for displaying various data to the surgeon 30 via the head-mounted display 32 and/or the external display 34; or the existence of an active connection with a given external machines/systems; and/or a user input that selects a procedure type via a graphic or other user interface system of the surgical microscope system 10; and/or the identity of the surgeon 30.

It will be appreciated that neural networks and the like may not be organized in blocks, such as the blocks included in FIGS. 2-5, and if the stage estimation/determination or other estimation/determination described herein, such as an estimated/determined current required illumination, is implemented using machine learning then the neural network may be represented by a black box receiving many inputs, and generating an output representing the estimated/determined stage, or the estimated/determined current required illumination respectively. Therefore, it will be appreciated that the blocks of FIGS. 2-5 are only for the sake of simplifying the understanding of the method and are not intended to limit the scope of the method. The steps may be performed in any order, simultaneously or in a black box type environment as described above.

Figure 6A:
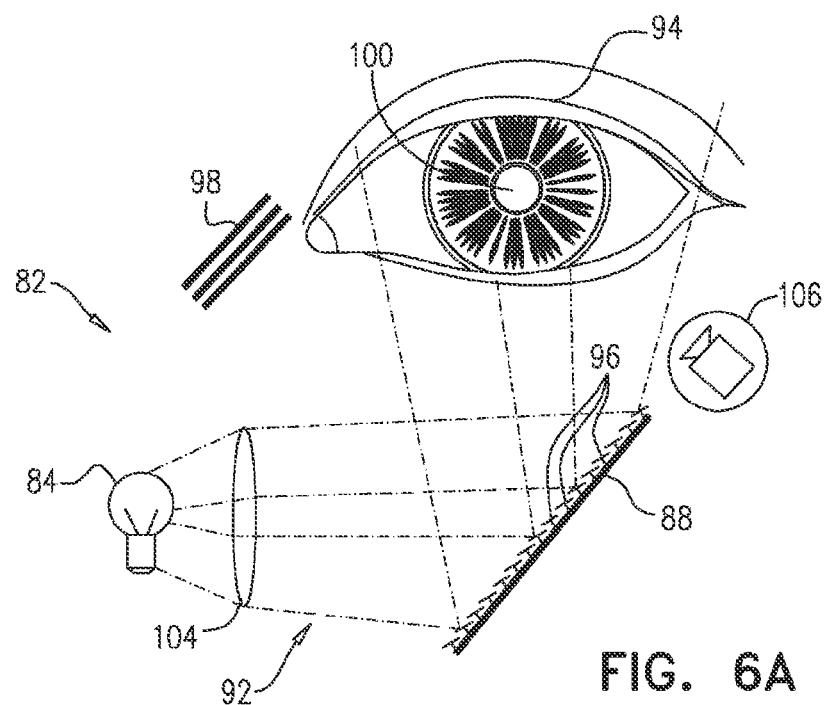
FIGS. 6a and 6b are partly pictorial, partly block diagram views of a dynamic light masking device configured to modify a spatial pattern of illumination from a single light source for use in the surgical microscope system of FIGS. 1a and 1 b.
Figure 6B:
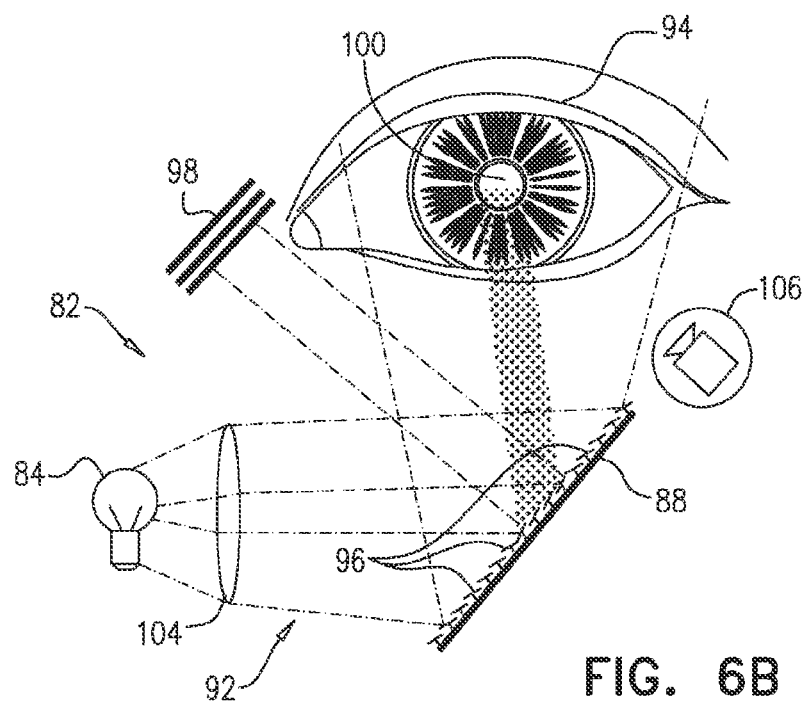

Reference is now made to FIGS. 6a and 6b, which are partly pictorial, partly block diagram views of a dynamic light masking device 82 configured to modify a spatial pattern of illumination from a single light source 84 for use in the surgical microscope system 10 of FIGS. 1*a* and 1*b*. Reference is also made to FIGS. 1*a* and 1*b*.

The adjustment to the illumination may include starting, stopping, dimming, increasing, or otherwise changing the illumination provided by the lighting unit 14. "Otherwise changing the illumination" includes changing a spatial and/or temporal pattern of the illumination. The various adjustments to the illumination are now described in more detail.

The lighting control system 12 may be configured to dim the illumination using any one or more of the following: (a) changing the temporal radiation pattern of the lighting unit 14 to a pulsing radiation pattern rather than a continuous one, thus reducing the total irradiation power; (b) electrically controlling a permanent liquid crystal shutter (LCS) disposed in an optical path of the lighting unit 14 wherein the opacity of the LCS and thus the illumination intensity may be controlled electronically; (c) automatically disposing a beam splitter into the optical path; and (d) automatically disposing a neutral-density filter into the optical path.

The adjustment to the illumination may include changing a spectrum of radiation of the illumination provided by the lighting unit 14, wherein the spectral power of the illumination may be modified in order to reduce the portion of the hazardous blue light within that illumination. An optical element that blocks the blue light may be automatically inserted in the optical path of the illuminating light (e.g. a long-pass optical filter or a dichroic mirror). Alternatively, or additionally, the lighting unit 14 may include two or more light sources, where the spectrum of one of the sources is less hazardous than of the other. The lighting unit 14 may be configured to automatically alternate between the sources in order to achieve momentarily reduction of hazardous light illumination (for instance the alternative light source could be in the near IR region, since imaging sensors usually operate in wavelengths up to 1050 nm). Therefore, the lighting unit 14 may be configured to change the spectrum of radiation of the illumination from a more harmful spectrum of radiation such as white light to a less harmful spectrum, such as IR light, that does not contain a harmful component, using any one or more of the following: disposing one or more optical components between the illumination source and the patient (e.g. a long-pass filter; a dichroic mirror; or a band-pass filter); switching between two or more sources of illumination (e.g., LEDs) having different radiation spectra (an example of this is described with reference to FIGS. 7*a* and 7*b*) and/or different radiation directions (i.e. flood vs. coaxial); or any other suitable optical arrangement.

Coaxial illumination may be based on IR light instead of visible light. In such a case image processing may be used to identify the pupil in the IR camera image and to artificially tint the illuminated area within the pupil with red color, so it appears to the surgeon as the standard red reflex and not monochromatic. The system may combine (or fuse) a color image (e.g. using visible flood light) with the IR image (using coaxial IR light) and display the red-tinted IR image inside the pupil and the color image outside the pupil.

Reducing the damaging illumination may be based on dynamically blocking only the light that illuminates the retina (or other sensitive body part), in the periods of time when it is not required for the surgical procedure. Therefore, the adjustment to the illumination provided by the lighting unit 14 may include modifying a spatial pattern of the illumination. Modifying the spatial pattern of the illumination may include dimming or stopping illumination of a first part of the region of illumination, or of a body part therein, while leaving the illumination of a second part of the region of illumination, or of the body part therein, unchanged. The lighting unit 14 may include the dynamic light masking device 82 configured to modify the spatial pattern of the illumination for example by modifying the illumination pattern that is reflected off the surface of the dynamic light masking device 82 or that is transferred through the dynamic light masking device 82. The dynamic light masking device 82 may include any one or more of the following to at least partially modify the pattern of illumination: a digital mirror device 88 shown in FIGS. 6*a* and 6*b*; a digital mirror device in an optical path of two radiation sources to selectively select between the two radiation sources shown in FIGS. 7*a* and 7*b*; a spatial light modulator; a movable spatial filter or mask or mirror or lens; and a liquid crystal shutter.

The use of the digital mirror device 88 is now described in more detail with reference to FIGS. 6*a* and 6*b*. The digital mirror device 88 is disposed in a path of a light beam 92 generated by the light source 84 that illuminates an eye 94 during the surgical procedure. The light beam 92 may be modified by a suitable configured lens 104. The digital mirror device 88 includes a plurality of computer controlled micro-mirrors 96 (only some are labeled for the sake of simplicity) which may be controlled by the controller 18 or any suitable processing resource. At least some of the micro-mirrors 96 may be in one of two angular positions or states. One is considered an 'ON' state, in which light that impinges on the micro-mirror 96 is reflected towards a pupil 100 of the eye 94 as shown in FIG. 6*a*. The other is considered an 'OFF' state in which light that impinges on the micro-mirrors 96 is reflected away from the pupil 100 and towards an optional beam blocker 98 as shown in FIG. 6*b*. The micro-mirrors 96 may support a spectrum of angular states but the above two states of the various states are used herein. The ON and OFF angles of each micro-mirrors 96 may be re-calibrated periodically or for each surgical procedure. A digital camera 106 may be configured to continuously or periodically capture a video of the eye 94 and transfer the data to the controller 18. The controller 18 analyzes the image(s) using an image processing algorithm and determines the location, size, and shape of the pupil 100 relative to the illuminated area. Using this information the controller 18 may configure the digital mirror device 88 to locally turn off the light that impinges on the pupil 100 by controlling the state of each micro-mirror 96 in the digital mirror device 88. Thus, the computer can dynamically control the illumination pattern that is illuminated onto the eye 94.

The determination of which of the micro-mirrors 96 are illuminating which areas in the surgical field may be accomplished in different ways. One method is to switch different groups of the micro-mirrors 96 on and off and analyze the image taken by the digital camera 106. Another method is based on pre-calibration of the position and orientation of the digital camera 106 relative to the digital mirror device 88. It should be noted that in the second method, depth information may also be used and may be retrieved by using two calibrated cameras or a 3D sensor by way of example only.

Figure 7A:
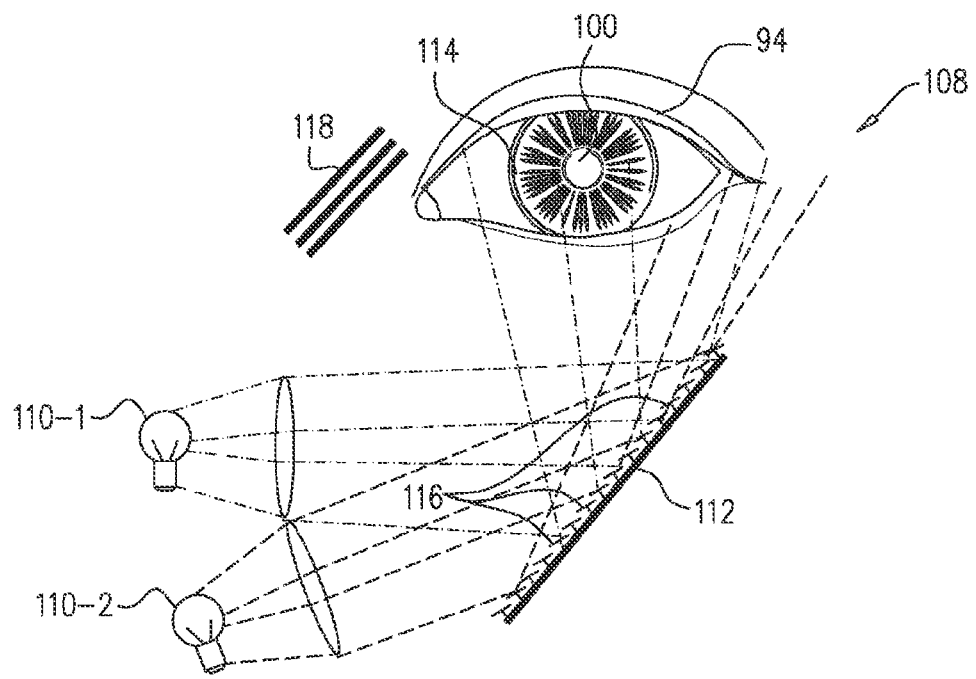
FIGS. 7a and 7b are partly pictorial, partly block diagram views of a dynamic light masking device configured to modify a spatial pattern of illumination from two different light sources for use in the surgical microscope system of FIGS. 1a and 1b.
Figure 7B:
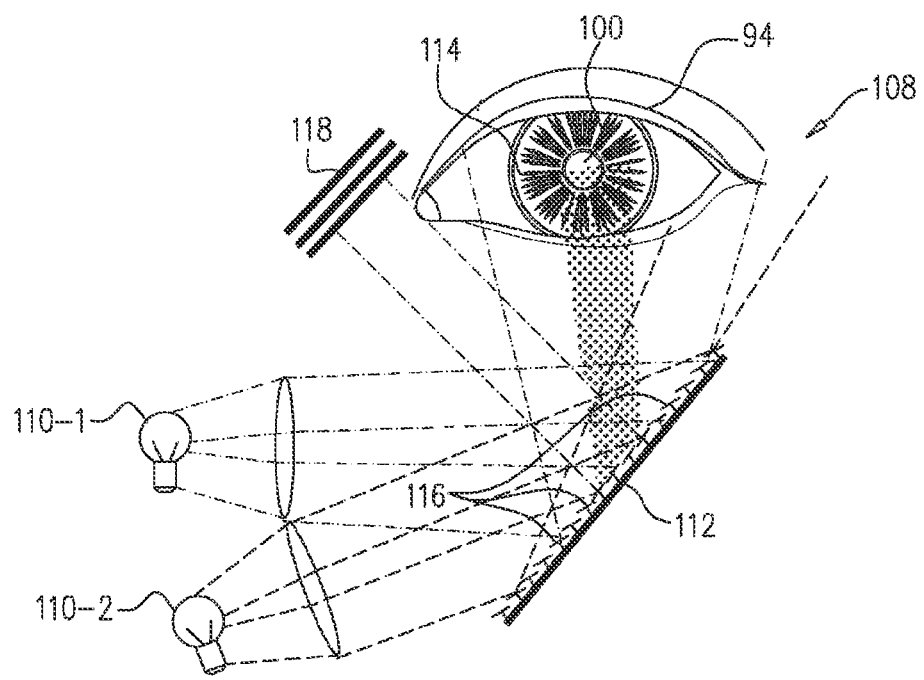

Reference is now made to FIGS. 7*a* and 7*b*, which are partly pictorial, partly block diagram views of a dynamic light masking device 108 configured to modify a spatial pattern of illumination from two different light sources 110 for use in the surgical microscope system 10 of FIGS. 1*a* and 1*b*. Reference is also made to FIGS. 1*a* and 1*b*. FIGS. 7*a* and 7*b* illustrate modifying the spatial pattern of the illumination by changing a radiation spectrum incident on a first part (e.g., the pupil 100) of the region of illumination, or of a body part therein (the eye 94), while leaving the radiation spectrum incident on a second part (e.g., the rest of the eye 94) of the region of illumination, or the body part therein, unchanged. The dynamic light masking device 108 may include a digital mirror device 112 in an optical path of the two radiation sources 110 to selectively select between the two radiation sources 110.

One of the light sources 110 may be a white light source 110-1 that is more hazardous to the eye 94, and the other light source 110 may be a less harmful light source 110-2. The less harmful light source 110-2 can be either a visible or an IR light source. The digital mirror device 112 may include two states, a state S1 and a state S2. In state S1, shown in FIG. 7*a* the pupil 100 and an iris 114 are both illuminated by the white light source 110-1. In state S2, shown in FIG. 7*b*, the pupil 100 is illuminated by the less harmful light source 110-2 and the iris 114 by the white light source 110-1 while some of the white light is reflected away from the eye in the direction of a beam blocker 118. The digital mirror device 112 includes a plurality of micro-mirrors 116 (only some labeled for the sake of simplicity) which may be individually controlled by the controller 18 to selectively generate state S1 or state S2.

The controller 18 may be configured to selectively change states from S1 to S2 to provide spatial pattern modification and optionally temporal pattern modification. For example, the controller 18 may be configured to illuminate the retina with white light once every several imaging cycles and with less harmful light during the rest of the imaging cycles (i.e. temporal modulation). In this way, continuous imaging of the retina may be achieved, but the overall light hazard is reduced. By way of an additional example, the controller 18 may be configured to select state S1 when the surgeon 30 is looking at the retina or the pupil 100 or has tools in the pupil 100 region and select state S2 at other times.

It should be noted that the use of IR or other non-visible light assumes that the surgeon 30 is watching a digital image of the surgical field either using the head-mounted display 32 or the external display 34. Using an IR light source is generally not used when the surgeon 30 is looking directly at the surgical field, with or without optics.

It should also be noted that the dynamic light masking device 82 of FIGS. 6*a* and 6*b* and the dynamic light masking device 86 may also enable illuminating various regions of the surgical field with various intensities. This may allow achieving an image with a better dynamic range, i.e., reducing saturation in bright areas of the image while imaging dark areas with high detail. A computer algorithm may be used to find saturated areas in the image. Saturated areas often occur because the irradiation power that is required to image the region of illumination is such that other areas in the image that might be bright or highly reflective saturate. The algorithm may locally eliminate the local saturations by projecting an uneven illumination across the image.

Figure 8:
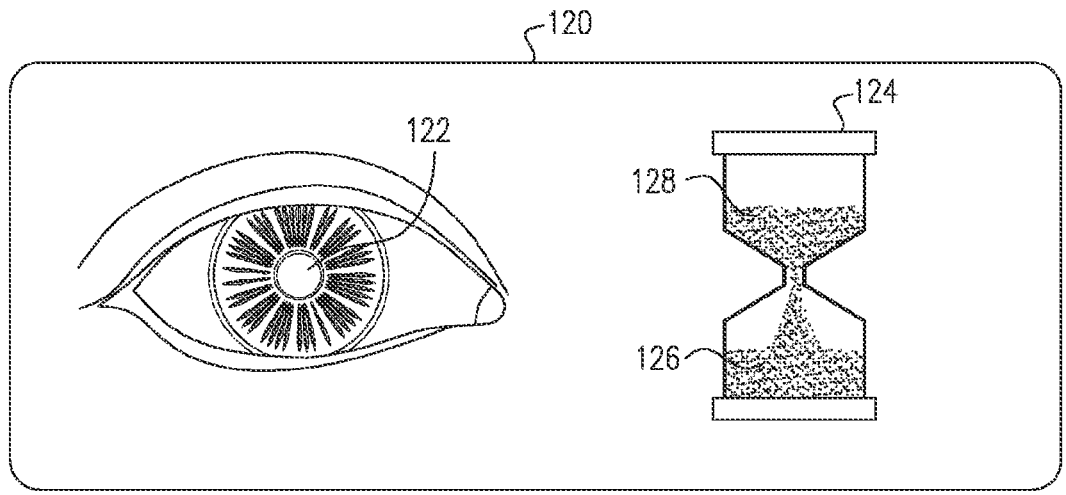
FIG. 8 is a pictorial view of a display showing a body part and an indication of an amount of radiation that has entered the body part for use with the surgical microscope system of FIGS. 1a and 1b.

Reference is now made to FIG. 8, which is a pictorial view of a display 120 showing a body part 122 and an indication 124 of an amount of radiation that has been irradiated on the body part for use with the surgical microscope system 10 of FIGS. 1*a* and 1*b*. Reference is also made to FIGS. 1*a* and 1*b*. The surgical microscope system 10 may be configured to continuously detect whether light was irradiated on the body part 122 (e.g., a patient's pupil) and monitor the illumination levels during these periods of time. Indications of the accumulated levels of weighted harmful light exposure may be brought to the attention of the surgeon 30 via the indication 124 which may also indicate a limit of allowed or recommended radiation in accordance with a standard. A software application may calculate accumulated harmful light exposure to a certain body part. The software application may take into account the exact time periods when the body part is illuminated, and the illumination power in each period. The software application may take into account the spectrum of each light source using a spectral weighted function to accurately accumulate the harmful light portion of each light source. Weighted spectral function is described, for example, in regulatory documents such as ANSI Z80.36-2016. The software application may analyze the real-time image of the eye to determine what portion of the illumination incident on the eye is incident on the retina. For example, the software application may take into account the size of the pupil and the opacity of the eye. It should be noted that phototoxicity damage during ophthalmic surgery occurs mostly in retinal cells. As described above, light can harm the body in various ways, for example, but not limited to, by thermal heating. Alternatively, or additionally, exposure to thermal heating due to illumination may also be determined and indicated by the surgical microscope system 10. For example, the hour-glass indicator 124 shown in FIG. 8 may indicate a cumulative light exposure (by a shading 126 in the bottom of the hour-glass) and a remaining allowed exposure (by a shading 128 in the top of the hour-glass). It will be appreciated that the display 120 may include more than one indicator 124 indicating light exposure compared to a standard for one or more different radiation spectra. The indicator(s) 124 may be disposed on any part of the display 120 and using any suitable format. The display 120 may be part of the head-mounted display 32 or the external display 34, by way of example only.

Figure 9:
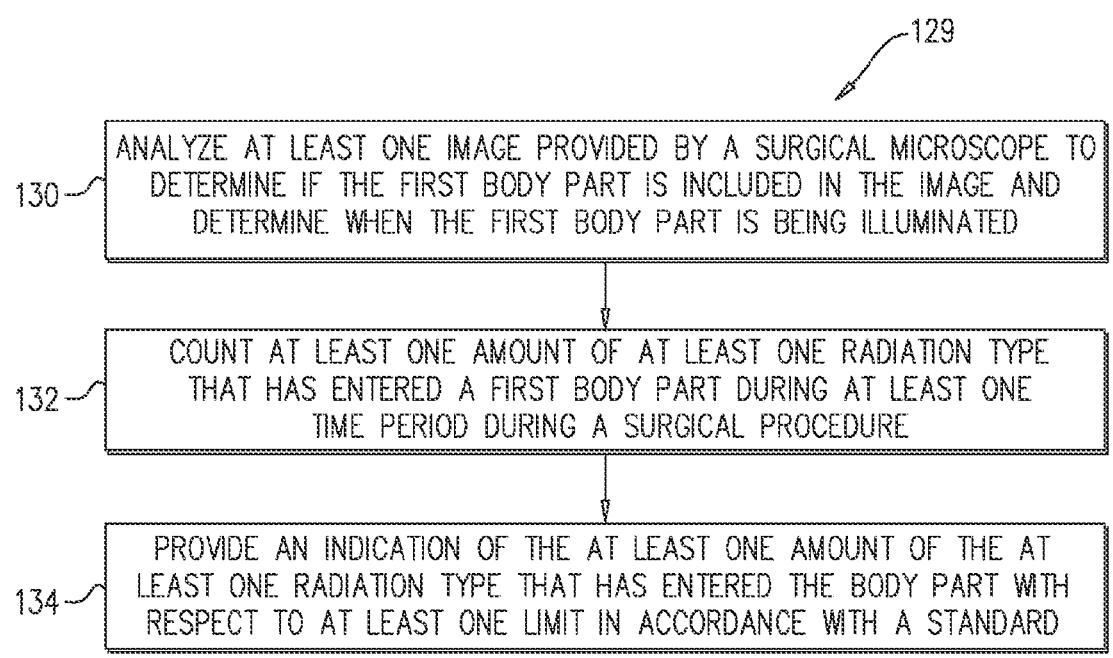
FIG. 9 is a flowchart including exemplary steps in a method of monitoring an amount of radiation that has entered a body part for use with the surgical microscope system of FIGS. 1a and 1b.

Reference is now made to FIG. 9, which is a flowchart 129 including exemplary steps in a method of monitoring an amount of radiated energy that has entered the body part 122 for use with the surgical microscope system 10 of FIGS. 1*a* and 1*b*. Reference is also made to FIGS. 1*a* and 1*b*. The controller 18 may be configured to analyze (block 130) at least one image provided by the surgical microscope system 10 to determine if the body part 122 is included in the image and determine when the body part 122 is being illuminated. The counter 22 may be configured to count (block 132) at least one amount of at least one radiation spectrum that has irradiate the body part 122 during at least one time period during the surgical procedure. The controller 18 may be configured to provide (block 134), to an output or storage device (e.g., the head-mounted display 32, the external display 34, hard-drive, etc.) the indication 124 of the at least one amount of the at least one radiation spectrum that has entered the body part 122 during the at least one time period with respect to at least one limit of allowed radiation in accordance with a standard. The indication 124 may include any one or more of the following: a recorded message; an audible indication; a textual and/or numeric and/or symbolic indicator (such as an hour glass indicator, a bar level indicator, etc.) displayed in the head-mounted display, or on any other display (e.g. monitor 34).

When the amount of radiation approaches its limit, the surgical microscope system 10 may automatically reduce, or offer the surgeon to manually reduce, the illumination and work with degraded performance. The surgical microscope system 10 may perform one or more compensatory actions to retain image brightness while degrading other image characteristics such as: opening a shutter of the image capture unit 16 allowing a reduction in the illumination but degrading the depth of field; increasing a sensor integration time of the image capture unit 16 which reduces the frame rate leading to a smearing of moving elements in the image; Using less harmful light, optionally while compromising the quality of the colors in the captured image; alternating between white light and less harmful light (e.g., IR light) where color compensation may be made to the frames captured with less harmful light using white-light-captured frames; changing the radiation spectrum by using a filter or changing the light source or any other suitable method; and increasing a sensor gain of the image capture unit 16 elevating noise levels in the image (e.g., snow-like effects). Therefore, in response to determining the adjustment to the illumination provided by the lighting unit 14, the controller 18 may be configured to send a signal to the image capture unit 16 to compensate for the adjustment by any one or more of the following: adjusting an opening of the shutter of the image capture unit 16; increasing an integration time of the sensor of the image capture unit 16; using a color correction module to compensate for color loss; and/or increasing a gain of the sensor.

Figure 10:
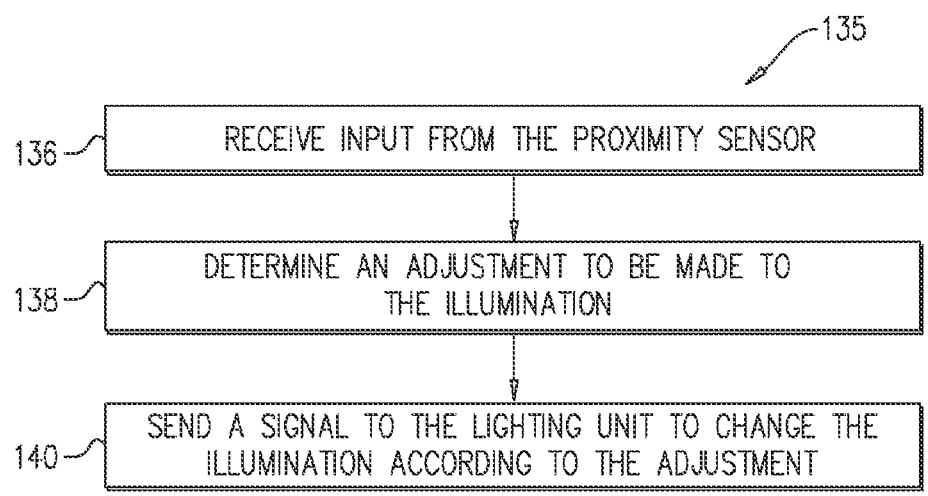
FIG. 10 is a flowchart including exemplary steps in another method of operation of the surgical microscope system of FIGS. 1a and 1b.

Reference is now made to FIG. 10, which is a flowchart 135 including exemplary steps in another method of operation of the surgical microscope system 10 of FIGS. 1*a* and 1*b*. Reference is also made to FIGS. 1*a* and 1*b*. The controller 18 may be configured to receive (block 136) input from a proximity sensor. The input provides an indication of whether or not the surgeon 30 is in proximity to an eyepiece (s) through which image data originating from the surgical microscope system 10 can be viewed. The controller 18 (FIGS. 1*a* and 1*b*) may be configured to determine (block 138) an adjustment to be made to the illumination provided by the lighting unit 14 based on whether or not the surgeon 30 is in proximity to the eyepiece(s). The controller 18 (FIGS. 1*a* and 1*b*) may be configured, in response to determining the adjustment, to send (block 140) a signal to the lighting unit 14 to change the illumination according to the adjustment.

It is to be noted that although reference is made herein to a proximity sensor, other/additional sensors can be used to determine whether or not the surgeon 30 is in proximity to an eyepiece(s) through which image data originating from the surgical microscope system 10 can be viewed. For example, a touch sensor can be used, by placing it at a position on the eyepiece so that when the surgeon 30 is viewing the image data therethrough, the surgeon touches the touch sensor. Another example is using a camera(s) to monitor the position of the surgeon's 30 head and using image analysis to determine if the surgeon is looking through the eyepiece.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting.

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

It will be appreciated by persons skilled in the art that the present disclosure is not limited by what has been particularly shown and described hereinabove. Rather the scope of the disclosure is defined by the appended claims and equivalents thereof.

The invention claimed is:

1. A system for adjustment of illumination in a surgical procedure, the system comprising a controller configured for:
   one or more of: (a) motion detection for detecting motion within a surgical field; and/or (b) tool detection and/or identification for detecting and/or identifying one or more surgical tools within the surgical field;
   determining that a user has no need for illumination of a region of illumination provided by a lighting unit for a surgical microscope when no motion is detected in the surgical field and/or no surgical tools are present within the surgical field; and
   in response to determining that the user has no need for the illumination of the region of illumination, sending a signal to the lighting unit to change the illumination provided by the lighting unit by at least one of the following:
   changing an intensity of the illumination;
   changing a spectrum of radiation of the illumination;
   switching between flood illumination and coaxial illumination;
   modifying a spatial pattern of the illumination,
   wherein the motion detection and/or the tool detection and/or identification are based on at least one image captured by at least one sensor.

2. The system according to claim 1, wherein the controller is further configured to:
   determine that there is a need for illumination of the region of illumination when motion and/or one or more surgical tools are detected within the surgical field,
   determine an adjustment to be made to the illumination provided by the lighting unit based on the motion detection and/or tool detection and/or identification;
   in response to determining the adjustment, send a signal to the lighting unit to change the illumination according to the determined adjustment.

3. The system according to claim 2, wherein the adjustment is determined also based on a confidence score calculated by one or more of: the motion detection, the tool detection and/or the specific tool identification.

4. The system according to claim 2, wherein the adjustment is best fitted for a region around a tool.

5. The system according to claim 1, wherein a first Field-of-View (FOV) of the at least one sensor is larger than a second FOV displayed to the surgeon, the second FOV is included in the first FOV, thereby enabling detecting the motion and/or the tool in a part of the first FOV external to the second FOV.

6. The system according to claim 5, wherein the second FOV is also imaged from said at least one sensor.

7. The system according to claim 1, wherein the controller is further configured to provide an indication of at least one amount of at least one radiation spectrum that has been irradiated on a first body part during at least one time period.

8. A method-for adjustment of illumination in a surgical procedure, the method comprising:
   performing one or more of: (a) motion detection for detecting motion within a surgical field; and/or (b) tool detection and/or identification, for detecting and/or identifying one or more surgical tools within the surgical field;
   determining that a user has no need for illumination of a region of illumination provided by a lighting unit for a surgical microscope when no motion is detected in the surgical field and/or no surgical tools are present within the surgical field; and in response to determining that the user has no need for the illumination of the region of illumination, sending a signal to the lighting unit to change the illumination provided by the lighting unit by at least one of the following:

changing an intensity of the illumination;

changing a spectrum of radiation of the illumination;

switching between flood illumination and coaxial illumination;

modifying a spatial pattern of the illumination.

9. The method according to claim 8, wherein the motion detection and/or the tool detection and/or identification is based on image analysis of at least one image captured by at least one sensor.

10. The method according to claim 9, wherein a first Field-of-View (FOV) of the at least one sensor is larger than a second FOV displayed to the surgeon, the second FOV is included in the first FOV, thereby enabling detecting the motion and/or the tool in a part of the first FOV external to the second FOV.

11. The method according to claim 10, wherein the first FOV and the second FOV are imaged from said first-sensor.

12. The method according to claim 8 further comprising:
determining that there is a need for illumination of the region of illumination when motion and/or one or more surgical tools are detected within the surgical field,
determining an adjustment to be made to the illumination provided by the lighting unit based on the motion detection and/or tool detection and/or identification;
in response to determining the adjustment, sending a signal to the lighting unit to change the illumination according to the determined adjustment.

13. The method according to claim 12, wherein the adjustment is determined also based on a confidence score calculated for the estimated lighting need.

14. The method according to claim 12, wherein the adjustment is best fitted for a region around a tool.

15. The method according to claim 8, further comprising providing an indication of at least one amount of at least one radiation spectrum that has been irradiated on a first body part during at least one time period.

16. A software product, comprising a non-transient computer-readable medium in which program instructions are stored, which instructions, when read by a central processing unit (CPU), cause the CPU to:
perform one or more of: (a) motion detection for detecting motion within a surgical field; and/or (b) tool detection and/or identification for detecting and/or identifying one or more surgical tools within the surgical field;
wherein the motion detection and/or the tool detection and/or identification are based on an image captured by at least one sensor; and
determine that a user has no need for illumination of a region of illumination provided by a lighting unit for a surgical microscope when no motion is detected in the surgical field and/or no surgical tools are present within the surgical field; and
in response to determining that the user has no need for the illumination of the region of illumination, sending a signal to the lighting unit to change the illumination provided by the lighting unit by at least one of the following:

changing an intensity of the illumination;

changing a spectrum of radiation of the illumination;

switching between flood illumination and coaxial illumination;

modifying a spatial pattern of the illumination.

17. A system for adjustment of illumination in a surgical procedure, the system comprising a controller configured to:
estimate or determine that a surgeon has no need for illumination of a region of illumination, provided by a lighting unit for a surgical microscope, during at least part of the surgical procedure when (a) the region of illumination is not being displayed, or (b) tracking data of the surgeon or a head mounted display indicates that the region of illumination is not being viewed by the surgeon; and
in response to determining that the surgeon has no need for illumination, send a signal to the lighting unit to reduce at least harmful illumination.

18. The system according to claim 17, wherein the controller is further configured to:
estimate or determine that there is a need of a surgeon for illumination provided by the lighting unit for the surgical microscope during at least part of the surgical procedure when (a) the region of illumination is being displayed, and/or (b) tracking data of the surgeon or a head mounted display indicates that the region of illumination is being viewed by the surgeon;
determine an adjustment to be made to the illumination; and
send a signal to the lighting unit to change the illumination according to the determined adjustment.

19. A method for adjustment of illumination in a surgical procedure, the method, comprising:
estimating or determining that a surgeon has no need for illumination of a region of illumination, provided by a lighting unit for a surgical microscope, during at least part of the surgical procedure, when (a) the region of illumination is not being displayed, or (b) tracking data of the surgeon or a head mounted display indicates that the region of illumination is not being viewed by the surgeon; and
in response to determining that the surgeon has no need for illumination, sending a signal to the lighting unit to reduce at least harmful illumination.

20. The method according to claim 19, further comprising:
estimating or determining that there is a need of the surgeon for illumination provided by the lighting unit for the surgical microscope during at least part of a surgical procedure when (a) the region of illumination is being displayed, and/or (b) tracking data of the surgeon or a head mounted display indicates that the region of illumination is being viewed by the surgeon;
determining an adjustment to be made to the illumination; and
sending a signal to the lighting unit to change the illumination according to the determined adjustment.

* * * * *